United States Patent

Yamamoto

(10) Patent No.: US 11,179,024 B2
(45) Date of Patent: Nov. 23, 2021

(54) ENDOSCOPE SYSTEM CAPABLE OF CORRECTING IMAGE, PROCESSOR DEVICE, AND METHOD FOR OPERATING ENDOSCOPE SYSTEM

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 574 days.

(21) Appl. No.: 16/056,560

(22) Filed: Aug. 7, 2018

(65) Prior Publication Data

US 2018/0368658 A1 Dec. 27, 2018

Related U.S. Application Data

(63) Continuation of application No. PCT/JP2016/086016, filed on Dec. 5, 2016.

(30) Foreign Application Priority Data

Mar. 7, 2016 (JP) .............................. JP2016-043420

(51) Int. Cl.
*A61B 1/00* (2006.01)
*G02B 23/24* (2006.01)
(Continued)

(52) U.S. Cl.
CPC ...... *A61B 1/00009* (2013.01); *A61B 1/00117* (2013.01); *A61B 1/00163* (2013.01);
(Continued)

(58) Field of Classification Search
None
See application file for complete search history.

(56) References Cited

U.S. PATENT DOCUMENTS 7,459,696 B2 * 12/2008 Schomaker ........ A61B 5/0059
250/458.1
8,060,188 B2 * 11/2011 Strane .................... A61B 5/413
600/473
(Continued)

FOREIGN PATENT DOCUMENTS

EP 2366327 9/2011
JP 2009142552 7/2009
(Continued)

OTHER PUBLICATIONS

"International Search Report (Form PCT/ISA/210) "of PCT/JP2016/086016 , dated Feb. 28, 2017, with English translation thereof, pp. 1-3.
(Continued)

*Primary Examiner* — Michael J Carey
*Assistant Examiner* — Minqiao Huang
(74) *Attorney, Agent, or Firm* — JCIPRNET

(57) ABSTRACT

An endoscope system includes a correction-value calculating unit that calculates a correction value of data to be used for calculation of biological information; an index-value calculating unit that calculates one type of index value or a plurality of types of index values to be used as a determination reference for determining whether the correction value is to be calculated or whether the correction value is to be used; a display unit that displays the one type of index value or the plurality of types of index values; an input unit that inputs an instruction for calculating the correction value or an instruction for executing correction by using the correction value; and a correction unit that, if the correction-value calculating unit calculates the correction value in response to the instruction for calculating the correction value or if the instruction for executing correction is issued, executes correction by using the correction value.

12 Claims, 16 Drawing Sheets

(51) Int. Cl.
*A61B 1/04* (2006.01)
*A61B 1/06* (2006.01)

(52) U.S. Cl.
CPC ..... *G02B 23/2407* (2013.01); *G02B 23/2484* (2013.01); *A61B 1/04* (2013.01); *A61B 1/0661* (2013.01); *G02B 23/2469* (2013.01)

(56) References Cited

U.S. PATENT DOCUMENTS

| | | | | |
|---|---|---|---|---|
| 8,382,666 | B1* | 2/2013 | Mao | A61B 5/14552 600/202 |
| 8,644,911 | B1* | 2/2014 | Panasyuk | A61B 5/0075 600/473 |
| 2010/0016666 | A1* | 1/2010 | Hasegawa | A61B 34/71 600/118 |
| 2010/0177181 | A1* | 7/2010 | Ayame | A61B 1/042 348/71 |
| 2012/0059239 | A1* | 3/2012 | Yamaguchi | A61B 6/5229 600/407 |
| 2012/0120216 | A1 | 5/2012 | Morita | |
| 2012/0265041 | A1* | 10/2012 | Yamaguchi | A61B 1/0653 600/328 |
| 2012/0307132 | A1* | 12/2012 | Fan | H04N 5/238 348/348 |
| 2013/0030268 | A1* | 1/2013 | Saito | A61B 1/05 600/325 |
| 2013/0096392 | A1* | 4/2013 | Adams | A61B 5/0064 600/301 |
| 2014/0152790 | A1* | 6/2014 | Saito | A61B 1/0005 348/68 |
| 2014/0184769 | A1* | 7/2014 | Ishihara | G06T 5/50 348/68 |
| 2014/0185907 | A1* | 7/2014 | Chiba | A61B 1/00009 382/134 |
| 2015/0201871 | A1* | 7/2015 | Shiraishi | A61B 5/1459 600/339 |
| 2015/0208958 | A1* | 7/2015 | Kaku | A61B 1/0638 600/339 |
| 2015/0216460 | A1* | 8/2015 | Shigeta | A61B 1/05 600/339 |
| 2015/0238086 | A1* | 8/2015 | Saito | A61B 1/0638 600/339 |
| 2015/0324983 | A1* | 11/2015 | Takasugi | A61B 1/0002 382/128 |
| 2015/0366444 | A1* | 12/2015 | Morimoto | A61B 5/1459 600/339 |
| 2016/0058274 | A1* | 3/2016 | Chiba | A61B 5/14546 600/328 |
| 2016/0120449 | A1* | 5/2016 | Chiba | A61B 5/1459 600/311 |
| 2016/0146723 | A1* | 5/2016 | Chiba | G01N 33/4833 250/208.1 |
| 2016/0183774 | A1* | 6/2016 | Shiraishi | A61B 1/0684 600/317 |
| 2016/0259159 | A1* | 9/2016 | Matsui | G02B 23/26 |
| 2016/0287061 | A1* | 10/2016 | Shigeta | A61B 1/0638 |
| 2016/0353972 | A1* | 12/2016 | Yano | H04N 5/2256 |
| 2017/0014055 | A1* | 1/2017 | Otani | A61B 1/0653 |

FOREIGN PATENT DOCUMENTS

| | | |
|---|---|---|
| JP | 2013022341 | 2/2013 |
| JP | 5562808 | 7/2014 |
| JP | 2015139657 | 8/2015 |

OTHER PUBLICATIONS

"Written Opinion of the International Searching Authority (Form PCT/ISA/237)" of PCT/JP2016/086016, dated Feb. 28, 2017, with English translation thereof, pp. 1-9.
"Search Report of Europe Counterpart Application", dated Feb. 15, 2019, p. 1-p. 7.

* cited by examiner

ENDOSCOPE SYSTEM CAPABLE OF CORRECTING IMAGE, PROCESSOR DEVICE, AND METHOD FOR OPERATING ENDOSCOPE SYSTEM

CROSS-REFERENCE TO RELATED APPLICATIONS

This application is a Continuation of PCT International Application No. PCT/JP2016/86016, filed on Dec. 5, 2016, which claims priority under 35 U.S.C. § 119(a) to Japanese Patent Application No. 2016-043420, filed on Mar. 7, 2016. Each of the above application(s) is hereby expressly incorporated by reference, in its entirety, into the present application.

BACKGROUND OF THE INVENTION

1. Field of the Invention

The present invention relates to an endoscope system, a processor device, and a method for operating the endoscope system. The endoscope system performs computation by using an endoscope image of an observation target captured by an endoscope.

2. Description of the Related Art

In the medical field, diagnosis is typically made by using an endoscope system including a light source device, an endoscope, and a processor device. In particular, a typically used endoscope system not only obtains an endoscope image of an observation target captured by an endoscope, but also generates and displays an image to be displayed (hereinafter referred to as an observation image), in which a tissue such as a blood vessel or a structure such as a duct structure is emphasized, by using the endoscope image. In recent years, an endoscope system that obtains biological information by using an endoscope image is also used. A lesion part is now diagnosed on the basis of, for example, the oxygen saturation level (biological information) of blood hemoglobin. In a method, a plurality of endoscope images are obtained by irradiating an observation target with, for example, light in a wavelength range for which the absorption coefficients of oxyhemoglobin and deoxyhemoglobin are different, and predetermined computation is performed by using the plurality of endoscope images to calculate the oxygen saturation level (JP2013-022341A and JP2015-139657A).

The biological information such as the oxygen saturation level may differ as a result of a difference of the part such as the gullet, stomach, or large intestine, or a patient's individual difference such as the patient's sex or age. Accordingly, in the endoscope system according to JP2013-022341A, data to be used for calculation of the oxygen saturation level is corrected (calibration is performed) by using a captured endoscope image of a patient and a part to be actually observed, so that the accurate oxygen saturation level can be calculated regardless of the difference of the part to be observed, the patient's individual difference, and the like. In addition, in the endoscope system according to JP2015-139657A, the current oxygen saturation level is compared with the oxygen saturation level in the past, and the calculated oxygen saturation level is corrected so that the accurate oxygen saturation level can be calculated.

SUMMARY OF THE INVENTION

In order to correct the data to be used for calculation of the biological information such as the oxygen saturation level or the like, as a matter of course, it is necessary to obtain a correction value that represents the degree of correction. For example, if the oxygen saturation level is calculated as the biological information, except for a case in which data of patients and parts such as the oxygen saturation level in the past is accumulated as in the endoscope system in JP2015-139657A, typically, the correction value has to be obtained by using an endoscope image of a patient captured in real time as in the endoscope system in JP2013-022341A.

If the correction value is inaccurate, calculation of the biological information by using data or the like that has been corrected by using the inaccurate correction value generates, as a matter of course, inaccurate biological information. Accordingly, an endoscope image to be used for calculation of the correction value (hereinafter this image will be referred to as a correction-value-calculation image) has to be an image of an observation target captured under appropriate conditions where the calculation error of the correction value falls within an allowable range.

However, when a correction-value-calculation image is obtained, it is difficult to determine in real time whether the image capturing conditions are appropriate. For example, if an endoscope image of an observation target captured under a situation where the observation target is moving is used as the correction-value-calculation image, the calculation error of the correction value is increased. Therefore, it is preferable that an endoscope image of an observation target captured under a situation where the observation target is not moving be used as the correction-value-calculation image. However, it is not possible to stop the movement of the observation target, which is a living body. Accordingly, it is necessary to determine in real time the degree of movement that can be allowed at the time of calculation of the correction value as image capturing conditions for obtaining the correction-value-calculation image. This determination is made only by those who are familiar with the method for calculating the correction value or the like and thus is difficult for a typical physician or the like who uses the endoscope system. The same applies to other image capturing conditions, such as the amount of illumination light.

An object of the present invention is to provide an endoscope system that supports determination as to whether the image capturing conditions are appropriate when a correction-value-calculation image is obtained, a processor device, and a method for operating the endoscope system.

An endoscope system according to the present invention includes an image acquiring unit that acquires an endoscope image of an observation target captured by an endoscope; a correction-value calculating unit that calculates, by using the endoscope image, a correction value of the endoscope image, biological information to be calculated by using the endoscope image, or data to be used for calculation of the biological information; an index-value calculating unit that calculates, by using the endoscope image, one type of index value or a plurality of types of index values to be used as a determination reference for determining whether the correction value is to be calculated or whether the correction value is to be used; a display unit that displays the one type of index value or the plurality of types of index values; an input unit that inputs an instruction for calculating the correction value or an instruction for executing correction of the endoscope image, the biological information, or the data by using the correction value; and a correction unit that, if the correction-value calculating unit calculates the correction value in response to the instruction for calculating the correction value or if the instruction for executing correction is issued, corrects the endoscope image, the biological information, or the data by using the correction value.

The endoscope system preferably includes a determination unit that determines, by using the one type of index value or the plurality of types of index values, whether the correction value is to be calculated or whether the correction value is to be used. The display unit preferably displays a result of determination of the determination unit in addition to the one type of index value or the plurality of types of index values.

If the index-value calculating unit calculates the plurality of types of index values, the determination unit preferably determines, for each of the plurality of types of index values, whether the correction value is to be calculated or whether the correction value is to be used, and the display unit preferably displays a result of determination of the determination unit together with each of the plurality of types of index values.

The endoscope system preferably includes an improvement instructing unit that, if the determination unit determines that the correction value is not to be calculated or that the correction value is not to be used, causes the display unit to display an improvement instruction regarding image capturing conditions for the endoscope image.

After the improvement instruction has been displayed, the improvement instructing unit preferably performs improvement determination for determining whether the image capturing conditions have been improved and preferably causes the display unit to display a result of the improvement determination.

The image acquiring unit preferably acquires a plurality of endoscope images of the observation target captured by the endoscope at different timings, the correction-value calculating unit preferably calculates the correction value by using the plurality of endoscope images, and the index-value calculating unit preferably calculates the one type of index value or the plurality of types of index values by using one or more of the plurality of endoscope images.

The image acquiring unit preferably changes illumination light or irradiation conditions of the illumination light and preferably acquires the plurality of endoscope images of the observation target captured at different timings.

The image acquiring unit preferably acquires, as the plurality of endoscope images, a correction-value-calculation image to be used for calculation of the correction value and a biological-information-calculation image to be used for calculation of the biological information, the correction-value calculating unit preferably calculates the correction value by using the correction-value-calculation image among the plurality of endoscope images, and the index-value calculating unit preferably calculates the one type of index value or the plurality of types of index values by using the correction-value-calculation image among the plurality of endoscope images.

The image acquiring unit preferably acquires, as one of the plurality of endoscope images, the biological-information-calculation image to be used for calculation of the biological information, the correction-value calculating unit preferably calculates the correction value by using the biological-information-calculation image, and the index-value calculating unit preferably calculates the one type of index value or the plurality of types of index values by using the biological-information-calculation image used by the correction-value calculating unit for calculating the correction value.

The input unit is preferably an input screen displayed on the display unit or an operating unit.

The index-value calculating unit preferably calculates the one type of index value or the plurality of types of index values of a movement amount of the observation target compared between the plurality of endoscope images, a movement amount of the observation target in one of the plurality of endoscope images, brightness, a pixel value, presence or absence of an attached matter, or an amount of the attached matter.

A processor device according to the present invention includes an image acquiring unit that acquires an endoscope image of an observation target captured by an endoscope; a correction-value calculating unit that calculates, by using the endoscope image, a correction value of the endoscope image, biological information to be calculated by using the endoscope image, or data to be used for calculation of the biological information; an index-value calculating unit that calculates, by using the endoscope image, one type of index value or a plurality of types of index values to be used as a determination reference for determining whether the correction value is to be calculated or whether the correction value is to be used; a display control unit that causes a display unit to display the one type of index value or the plurality of types of index values; and a correction unit that, if the correction-value calculating unit calculates the correction value in response to the instruction for calculating the correction value or if the instruction for executing correction is issued, corrects the endoscope image, the biological information, or the data by using the correction value.

A method for operating an endoscope system according to the present invention includes a step in which an image acquiring unit acquires an endoscope image of an observation target captured by an endoscope; a step in which a correction-value calculating unit calculates, by using the endoscope image, a correction value of the endoscope image, biological information to be calculated by using the endoscope image, or data to be used for calculation of the biological information; a step in which an index-value calculating unit calculates, by using the endoscope image, one type of index value or a plurality of types of index values to be used as a determination reference for determining whether the correction value is to be calculated or whether the correction value is to be used; a step in which a display unit displays the one type of index value or the plurality of types of index values; and a step in which, if the correction-value calculating unit calculates the correction value in response to the instruction for calculating the correction value or if the instruction for executing correction is issued, a correction unit corrects the endoscope image, the biological information, or the data by using the correction value.

According to the endoscope system, the processor device, and the method for operating the endoscope system according to the present invention, an index value that is used as a determination reference for determining whether a correction value is to be calculated or whether the correction value is to be used is calculated and displayed on a display unit. Accordingly, it is possible to support determination as to whether the image capturing conditions are appropriate when a correction-value-calculation image is obtained.

DESCRIPTION OF THE PREFERRED EMBODIMENTS

First Embodiment

Figure 1:
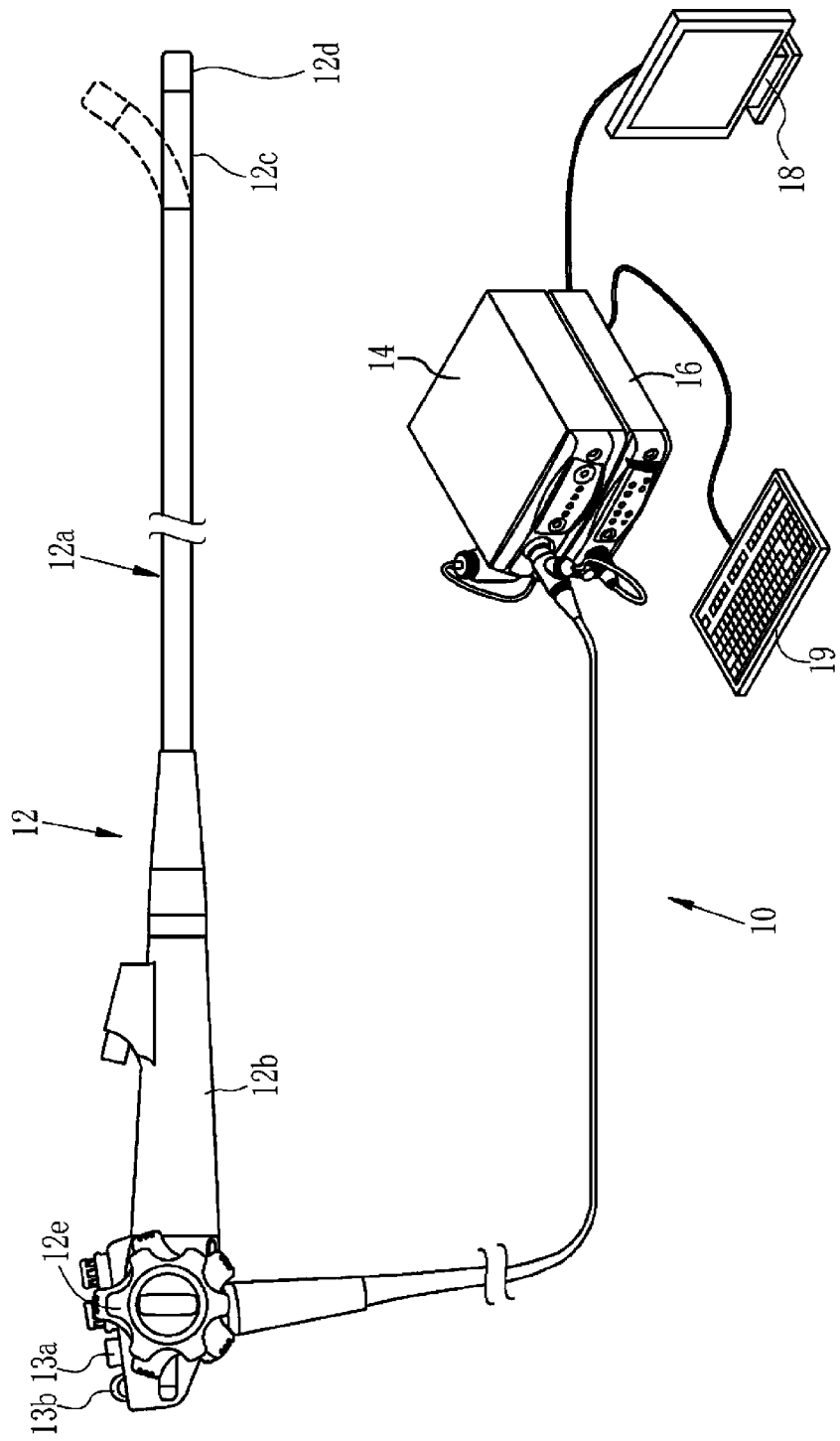
FIG. 1 is an external view of an endoscope system.

As illustrated in FIG. 1, an endoscope system 10 has an endoscope 12 that captures images of an observation target, a light source device 14, a processor device 16, a monitor 18 that is a display unit, and a console 19. The endoscope 12 is optically connected to the light source device 14 and is electrically connected to the processor device 16. The endoscope 12 has an insertion part 12a to be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result of the bending of the bending part 12c, the tip part 12d is oriented in a desired direction. Note that the tip part 12d is provided with a jet orifice (not illustrated) through which air, water, or the like is ejected toward the observation target.

In addition, the operating unit 12b is provided with, in addition to the angle knob 12e, a mode switch 13a and a zoom operating unit 13b. The mode switch 13a is used for operation of switching an observation mode. The endoscope system 10 has a normal observation mode and a special observation mode. The normal observation mode is an observation mode for displaying, on the monitor 18, an observation image with natural colors (hereinafter this observation image will be referred to as a normal observation image) obtained by capturing an image of the observation target by using white light as illumination light.

In the special observation mode, by using an endoscope image of the observation target captured by the endoscope 12, the biological information of the observation target is calculated and displayed, or, an observation image in which a specific tissue or structure of the observation target is, for example, emphasized is generated and displayed. Hereinafter, the special observation mode for calculating and displaying the biological information of the observation target will be referred to as a biological-information observation mode, and the special observation mode for generating and displaying an observation image in which a specific tissue or structure of the observation target is, for example, emphasized will be referred to as an emphasized observation mode. Note that these are examples, and in the special observation mode, it is possible to calculate and display the biological information of the observation target and to generate and display an observation image in which a specific tissue or structure of the observation target is, for example, emphasized.

The biological information is information about a living body that is not easily obtained by merely viewing a normal observation image, and is, for example, numerical information about the observation target, such as the oxygen saturation level or the density of a blood vessel. In addition, the phrase "a specific tissue or structure of the observation target is, for example, emphasized" in the emphasized observation mode includes, in addition to the emphasis or the like of one or more types of specific tissues or structures from among observable tissues or structures, the emphasis or the like of some of a type of specific tissue or structure having common properties. That is, in the emphasized observation mode, while a specific tissue such as a blood vessel is, for example, emphasized from among observable tissues or structures, depending on the setting, not all the blood vessels are, for example, emphasized, but only a blood vessel at a specific depth from a predetermined reference point on a mucous membrane or the like can be, for example, selectively emphasized. Alternatively, for example, in the emphasized observation mode, only blood vessels whose thickness is within a specific range can be, for example, selectively emphasized.

In addition, the special observation mode includes a correction operation in addition to an operation during which the biological information is calculated and displayed, or a specific tissue or structure is, for example, emphasized and displayed, by using an endoscope image as described above (hereinafter this operation will be referred to as a main operation). During the correction operation, an "endoscope image to be used during the main operation", "biological information to be calculated during the main operation", or "data to be used for calculation of biological information during the main operation" is corrected.

An endoscope image to be used for correction of the above "endoscope image to be used during the main operation", "biological information to be calculated during the main operation", or "data to be used for calculation of biological information during the main operation" during the correction operation is a correction-value-calculation image. In this embodiment, a plurality of endoscope images of the observation target captured by the endoscope 12 at different timings during the correction operation are correct-value calculation images.

Specifically, in a case of the biological-information observation mode, the "endoscope image to be used during the main operation" is an endoscope image to be used for calculation of the biological information during the main operation (hereinafter this image will be referred to as a biological-information-calculation image") or an endoscope image to be used for generation of an observation image in which the biological information that is calculated during the main operation is displayed. In addition, in a case of the emphasized observation mode, the "endoscope image to be used during the main operation" is an endoscope image to be used for identification of a tissue or structure to be, for example, emphasized during the main operation or an endoscope image to be used for generation of an observation image in which the specific tissue or structure is, for example, emphasized during the main operation.

The "biological information to be calculated during the main operation" is biological information such as the oxygen saturation level that is calculated in a case in which the special observation mode is the biological-information observation mode. In addition, the "data to be used for calculation of biological information during the main operation" is data that is used for calculation of the biological information in addition to the endoscope image. For example, in a case in which the oxygen saturation level is calculated as the biological information, the data is a data table, a transition function, or the like for associating a computation value that is calculated by using a plurality endoscope images with the oxygen saturation level.

Note that the correction of the "endoscope image to be used during the main operation", the "biological information to be calculated during the main operation", or the "data to be used for calculation of biological information during the main operation" is calibration of the special observation mode that is performed for calculating the accurate biological information or for, for example, accurately emphasizing a specific tissue or structure.

In the biological-information observation mode, which is an example of the special observation mode, the endoscope system 10 performs computation by using an endoscope image and calculates target biological information by using data that is prepared in advance for associating the computation result with the biological information. This is the main operation in the biological-information observation mode. On the other hand, during the correction operation, the correction value is calculated by using an endoscope image. Subsequently, by using the calculated correction value, the "endoscope image to be used during the main operation", the "biological information to be calculated during the main operation", or the "data to be used for calculation of biological information during the main operation" is corrected. Thus, in a case of the biological-information observation mode, the biological information can be accurately calculated during the main operation. In addition, in a case of the emphasized observation mode, an observation image in which a specific tissue or structure is, for example, accurately emphasized can be generated and displayed.

In this embodiment below, the special observation mode is the biological-information observation mode in which the oxygen saturation level is calculated and displayed. That is, the special observation mode in this embodiment is an oxygen-saturation-level observation mode. In the oxygen-saturation-level observation mode, during the main operation, a computation value that is correlated with the oxygen saturation level is calculated by using a plurality of endoscope images. Subsequently, by using the calculated computation value and data that associates the computation value with the oxygen saturation level, the oxygen saturation level is calculated. Subsequently, by using a plurality of endoscope images and the calculated oxygen saturation level, an observation image in which the value of the oxygen saturation level is illustrated by using a pseudo color (hereinafter this observation image will be refereed to as an oxygen-saturation-level image 110 (see FIG. 9)) is generated and displayed. In addition, in the oxygen-saturation-level observation mode in this embodiment, during the correction operation, the correction value is calculated by using a plurality of endoscope images (correction-value-calculation images) of the observation target captured by the endoscope 12 at different timings. Subsequently, by using the calculated correction value, the data to be used for calculation of the oxygen saturation level during the main operation (i.e., the above "data that associates the computation value with the oxygen saturation level") is corrected.

The processor device 16 is electrically connected to the monitor 18 and the console 19. The monitor 18 outputs and displays observation images in the respective observation modes, image information accompanying the observation images, and the like. The console 19 is a part of an input unit 74 (see FIG. 2 or FIG. 3) serving as a user interface that receives an input operation for setting functions and the like. Note that an external recording unit (omitted from illustration) for recording images, image information, and the like may be connected to the processor device 16.

Figure 2:
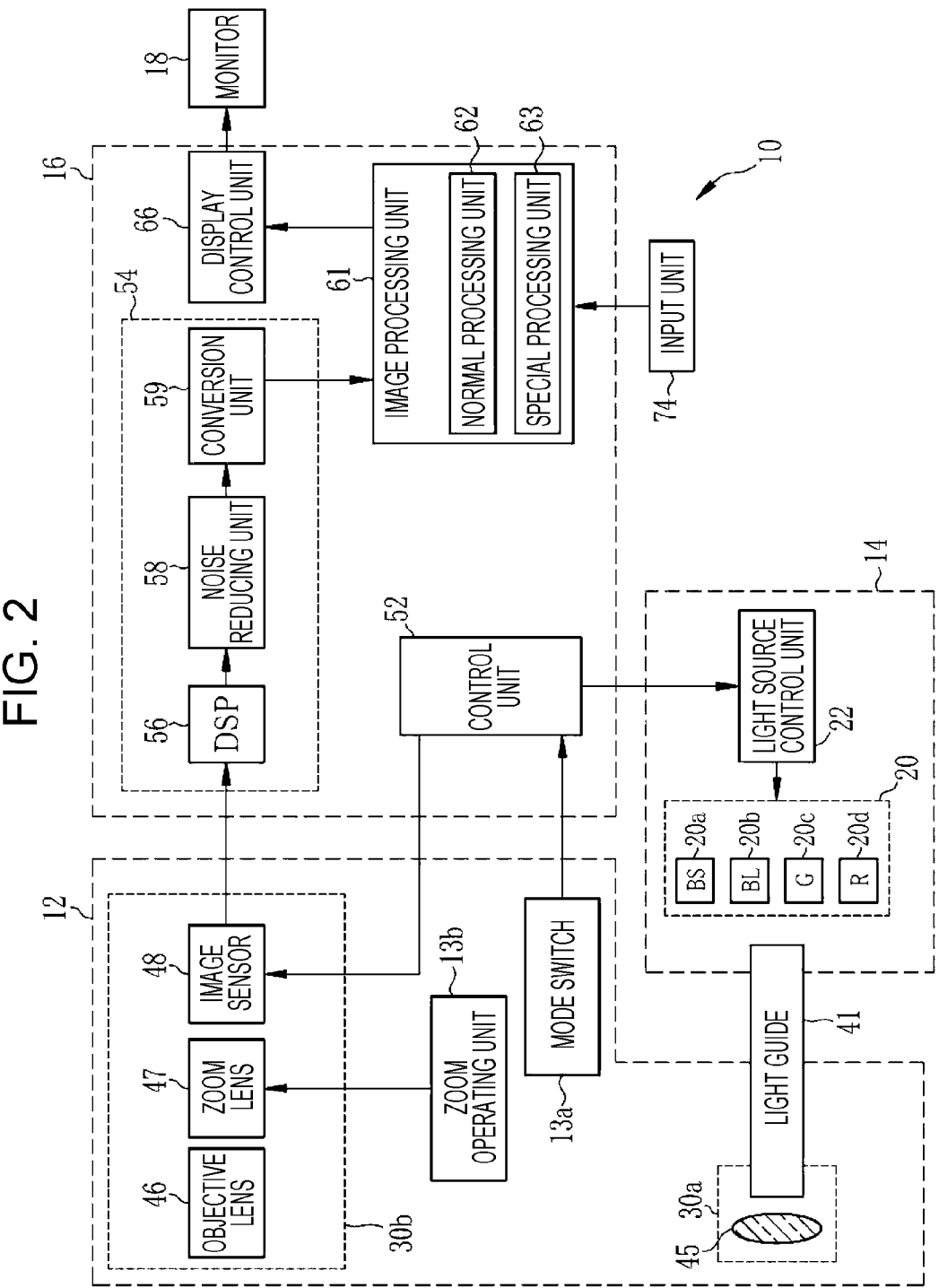
FIG. 2 is a block diagram of the endoscope system.

As illustrated in FIG. 2, the light source device 14 includes a light source unit 20 that emits illumination light and a light source control unit 22 that controls driving of the light source unit 20.

The light source unit 20 includes four light sources, which are a BS light source 20a, a BL light source 20b, a G light source 20c, and an R light source 20d. In this embodiment, the BS light source 20a, the BL light source 20b, the G light source 20c, and the R light source 20d are light emitting diodes (LEDs). For the light source unit 20, instead of these LEDs, a combination of a laser diode (LD), a fluorescent body, and a band limiting filter, a combination of a lamp such as a xenon lamp and a band limiting filter, or the like can be used.

The BS light source 20a is a blue light source that emits first blue light BS with a center wavelength of about 450±10 nm and a wavelength range of about 420 nm to 500 nm. The BL light source 20b is a blue light source that emits blue, so-called narrow-band light (hereinafter referred to as second blue light BL) with a center wavelength and a wavelength range of about 470±10 nm. The G light source 20c is a green light source that emits green light G with a center wavelength of about 540±20 nm and a wavelength range of about 480 nm to 600 nm. The R light source 20d is a red light source that emits red light R with a center wavelength of about 640±20 nm and a wavelength range of about 600 nm to 650 nm.

The light source control unit 22 independently controls timings for turning on and off the respective light sources 20a to 20d constituting the light source unit 20, light emission amounts at the time of turning on, and the like. Under the control of the light source control unit 22, the light source unit 20 emits illumination light for normal observation to be used in the normal observation mode and illumination light for special observation to be used in the special observation mode.

In a case of the normal observation mode, the light source control unit 22 turns on the BS light source 20a, the G light source 20c, and the R light source 20d at the same time. Accordingly, the illumination light for normal observation is white light including the first blue light BS, the green light G, and the red light R. The white light herein includes pseudo white light that can be regarded as white light. In addition, in this embodiment, although the light source unit 20 continuously turns on the above white light in a case of the normal observation mode, the light source unit 20 may emit white light in accordance with an image capturing frame.

The illumination light for special observation includes illumination light for main operation to be used during the main operation, and illumination light for correction operation to be used during the correction operation. The illumination light for main operation and the illumination light for correction operation each include, in accordance with the actual embodiment of the special observation mode, light of one or more colors (a plurality of types of light with different wavelengths, wavelength ranges, or spectra). In addition, the illumination light for main operation may be different from or may be the same as the illumination light for correction operation depending on the actual embodiment of the special observation mode.

In the oxygen-saturation-level observation mode, which is the special observation mode in this embodiment, the light source control unit 22 alternately repeats the turning on and off of the light sources 20a to 20d by using a first pattern and a second pattern during the main operation. The first pattern is an emission pattern in which only the BL light source 20b is turned on. Accordingly, at the time of the first pattern, the second blue light BL is the illumination light for special observation. On the other hand, the second pattern is a pattern in which the BS light source 20a, the G light source 20c, and the R light source 20d are turned on at the same time. Accordingly, at the time of the second pattern, white light including the first blue light BS, the green light G, and the red light R is the illumination light for special observation. Therefore, in the oxygen-saturation-level observation mode, the second blue light BL and the white light are alternately emitted in accordance with the image capturing frame during the main operation.

In addition, the light source control unit 22 alternately repeats the turning on and off by using the first pattern and the second pattern in accordance with the image capturing frame also during the correction operation. Accordingly, in the oxygen-saturation-level observation mode, which is the special observation mode in this embodiment, the illumination light for main operation is the same as the illumination light for correction operation, and their emission patterns are also the same. The illumination light for correction operation that is the same as the illumination light for main operation is emitted also during the correction operation in this manner because the oxygen saturation level is calculated also during the correction operation, and, by using the oxygen saturation level calculated during the correction operation as the correction value, data to be used for calculation of the oxygen saturation level during main operation is corrected.

Illumination light emitted from the light source unit 20 enters a light guide 41. The light guide 41 is incorporated in the endoscope 12 and a universal cord, and the illumination light propagates therethrough to the tip part 12d of the endoscope 12. The universal cord is a cord connecting the endoscope 12, the light source device 14, and the processor device 16. Note that a multi-mode fiber can be used as the light guide 41. As an example, a small-diameter fiber cable having a core diameter of 105 µm, a clad diameter of 125 µm, and a diameter of Ø 0.3 to 0.5 mm including a protective layer serving as an outer skin can be used.

The tip part 12d of the endoscope 12 is provided with an illumination optical system 30a and an image capturing optical system 30b. The illumination optical system 30a has an illumination lens 45, and an observation target is irradiated with illumination light through the illumination lens 45. The image capturing optical system 30b has an objective lens 46, a zoom lens 47, and an image sensor 48. The image sensor 48 captures images of the observation target by using reflected light or the like (including, in addition to reflected light, scattered light, fluorescence emitted from the observation target, fluorescence caused by medicine that is, for example, given to the observation target, and the like) of illumination light returning from the observation target through the objective lens 46 and the zoom lens 47. Note that the zoom lens 47 is moved by operating the zoom operating unit 13b and zooms in or zooms out the observation target whose image is captured by the image sensor 48.

The image sensor 48 is a color sensor of the primary color system and includes three types of pixels: a B pixel (blue pixel) having a blue color filter, a G pixel (green pixel) having a green color filter, and an R pixel (red pixel) having a red color filter. The blue color filter mainly transmits light of a blue range, specifically light with a wavelength range of 380 to 560 nm. The transmittance of the blue color filter peaks at or around a wavelength from 460 to 470 nm. The green color filter mainly transmits light of a green range, specifically light with a wavelength range of 460 to 470 nm. The red color filter mainly transmits light of a red range, specifically light with a wavelength range of 580 to 760 nm.

When images of the observation target are captured by the image sensor 48, at most three types of endoscope images, which are a B image (blue image) obtained by image capturing at the B pixel, a G image (green image) obtained by image capturing at the G pixel, and an R image (red image) obtained by image capturing at the R pixel, can be obtained at the same time. In a case of the normal observation mode, the illumination light for normal observation to be used is white light, which includes blue, green, and red components, and accordingly, a B image, a G image, and an R image can be obtained in each image capturing frame.

On the other hand, the illumination light for special observation in the special observation mode in this embodiment is switched between the second blue light BL and white light formed of the first blue light BS, the green light G, and the red light R in each image capturing frame. Accordingly, in an image capturing frame in which the illumination light for special observation is the second blue light BL, only the B image is substantially obtained. In addition, in an image capturing frame in which the illumination light for special observation is white light, the B image, the G image, and the R image are obtained. Hereinafter, the B image obtained in an image capturing frame in which the illumination light for special observation is the second blue light BL will be referred to as a B1 image, and the B image, the G image, and the R image obtained in an image capturing frame in which the illumination light for special observation light is white light will be referred to as a B2 image, a G2 image, and an R2 image, respectively.

The B1 image, the B2 image, the G2 image, and the R2 image are endoscope images of the observation target captured by the endoscope 12 at different timings and may be referred to as multi-frame images in the relationship with respective image capturing timings. For example, in the oxygen-saturation-level observation mode in this embodiment, the B1 image, the B2 image, the G2 image, and the R2 image are each a multi-frame image. In addition, a plurality of multi-frame images are two or more endoscope images in which, for example, any one or more images from the B1 image, the B2 image, the G2 image, and the R2 images are combined.

Note that a charge coupled device (CCD) sensor or a complementary metal oxide semiconductor (CMOS) sensor can be used as the image sensor 48. In addition, although the image sensor 48 in this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially capturing images of the observation target by using illumination light of the respective colors such as BGR, images of the above respective colors can be obtained.

The processor device 16 has a control unit 52, an image acquiring unit 54, an image processing unit 61, and a display control unit 66. For example, the processor device 16 has a central processing unit (CPU), and the CPU serves as the control unit 52, the image acquiring unit 54, the image processing unit 61, and the display control unit 66.

In response to an input of a mode switching signal from the mode switch 13a, the control unit 52 inputs a control signal into the light source control unit 22 and the image sensor 48 to switch the observation mode. Besides, the control unit 52 generally controls the endoscope system 10 such as synchronization of an illumination-light irradiation timing and an image capturing timing, for example.

The image acquiring unit 54 acquires images of the observation target from the image sensor 48. In a case of the normal observation mode, the image acquiring unit 54 acquires a set of the B image, the G image, and the R image in each image capturing frame. In addition, in a case of the special observation mode, the image acquiring unit 54 acquires an image in accordance with the illumination light for special observation in each image capturing frame. For example, in a case of the special observation mode, the image acquiring unit 54 acquires a plurality of endoscope images of the observation target captured with different illumination light or different irradiation conditions of the illumination light at different timings. In a case of the oxygen-saturation-level observation mode, which is the special observation mode in this embodiment, the image acquiring unit 54 alternately acquires at least a set of a B1 image, a B2 image, a G2 image, and an R2 image in each image capturing frame.

The image acquiring unit 54 has a digital signal processor (DSP) 56, a noise reducing unit 58, and a conversion unit 59, and performs various kinds of processing on the acquired images by using these units.

The DSP 56 performs various kinds of processing on the acquired images, such as defect correction processing, offset processing, gain correction processing, linear matrix processing, gamma conversion processing, demosaicing processing, and YC conversion processing, as needed.

The defect correction processing is for correcting the pixel value of a pixel corresponding to a defective pixel of the image sensor 48. The offset processing is for setting an accurate zero level by reducing a dark current component from an image subjected to the defect correction processing. The gain correction processing is for adjusting the signal level of each image by multiplying the image subjected to the offset processing by a gain. The linear matrix processing increases the color reproducibility of an image subjected to the offset processing, and the gamma conversion processing is for adjusting the brightness and saturation of an image subjected to the linear matrix processing. The demosaicing processing (also referred to as isotropic processing or synchronization processing) is for interpolating the pixel value of a lacking pixel and is performed on an image subjected to the gamma conversion processing. The lacking pixel is a pixel without a pixel value as a result of arrangement of a pixel of another color in the image sensor 48 for the array of the color filters. For example, since the B image is obtained by capturing an image of the observation target by using the B pixel, there are no pixel values of pixels at positions corresponding to the G pixel and the R pixel in the image sensor 48. The demosaicing processing is for interpolating the B image and generating the pixel values of the pixels at positions corresponding to the G pixel and the R pixel in the image sensor 48. The YC conversion processing is for converting an image subjected to the demosaicing processing into a luminance channel Y, a chrominance channel Cb, and a chrominance channel Cr.

The noise reducing unit 58 performs noise reducing processing on the luminance channel Y, the chrominance channel Cb, and the chrominance channel Cr by using, for example, a moving average method, a median filter method, or the like. The conversion unit 59 re-converts the luminance channel Y, the chrominance channel Cb, and the chrominance channel Cr, which have been subjected to the noise reducing processing, into images of BGR colors again.

The image processing unit 61 has a normal processing unit 62 and a special processing unit 63. The normal processing unit 62 operates in the normal observation mode and performs color converting processing, color emphasizing processing, and structure emphasizing processing on a B image, a G image, and an R image in an image capturing frame, which have been subjected to the above processing, to generate a normal observation image. In the color converting processing, the images of BGR colors are subjected to 3×3 matrix processing, gradation transformation processing, three-dimensional look-up table (LUT) processing, and the like. The color emphasizing processing is for emphasizing the colors in an image, and the structure emphasizing processing is, for example, for emphasizing a tissue or a structure of the observation target, such as a blood vessel or a pit pattern. The display control unit 66 sequentially acquires the normal observation image from the normal processing unit 62 and converts the acquired normal observation image into an image in a format suitable for display to sequentially output and display the image to/on the monitor 18. Thus, in a case of the normal observation mode, a physician or the like can observe the observation target by using a motion picture of the normal observation image.

Figure 3:
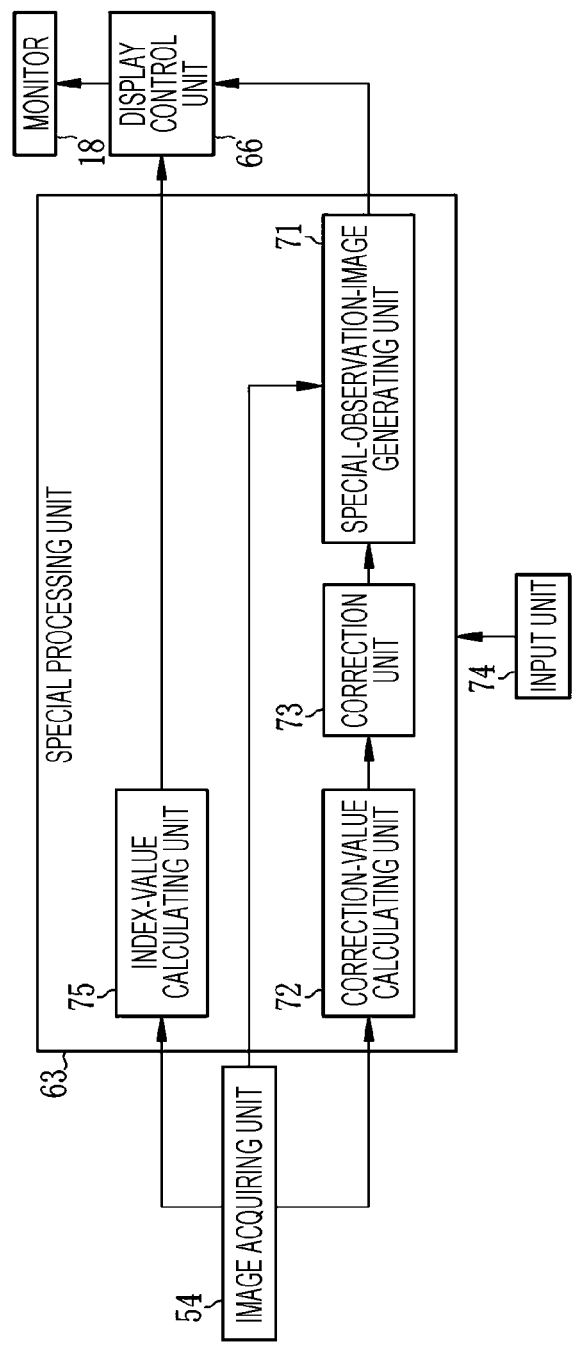
FIG. 3 is a block diagram of a special processing unit.

As illustrated in FIG. 3, the special processing unit 63 includes a special-observation-image generating unit 71, a correction-value calculating unit 72, a correction unit 73, and an index-value calculating unit 75.

During the main operation, the special-observation-image generating unit 71 generates an observation image in accordance with the actual embodiment of the special observation mode (hereinafter this image will be referred to as a special observation image) by using an endoscope image acquired from the image acquiring unit 54. In a case in which the special observation mode is the biological-information observation mode, the special-observation-image generating unit 71 calculates biological information by using the endoscope image and generates a special observation image representing the biological information (hereinafter this image will be referred to as a biological information image). In a case in which the special observation mode is the emphasized observation mode, by using the endoscope image, the special-observation-image generating unit 71, for example, extracts a specific tissue or structure (including processing for selecting or distinguishing the specific tissue or structure from other tissues or structures that are not, for example, emphasized) and generates a special observation image in which, for example, the extracted specific tissue or structure is, for example, emphasized (hereinafter this image will be referred to as an emphasized observation image).

In addition, during the correction operation, the special-observation-image generating unit 71 generates a natural observation image, instead of the above special observation image, by using an endoscope image. The natural observation image herein is an observation image in which a specific tissue or structure is, for example, not emphasized, and coloring or the like is not performed for displaying the biological information. That is, during the correction operation, the special-observation-image generating unit 71 generates an observation image 101 that is substantially the same as the normal observation image in the normal observation mode (hereinafter this image will be referred to as a "normal observation image", see FIG. 8).

The special-observation-image generating unit 71 causes the monitor 18 to display the generated special observation image or normal observation image 101 via the display control unit 66. That is, the monitor 18 displays the special observation image during the main operation and displays the normal observation image 101 during the correction operation. Note that the display control unit 66 causes the monitor 18 to display information related to the special observation image or the normal observation image 101, information supporting the diagnosis of a physician or the like, a button for input operation, and the like, as needed. For example, when displaying the oxygen-saturation-level image 110 on the monitor 18, the display control unit 66 causes the monitor 18 to display an indicator representing a correspondence relationship between a pseudo color and the oxygen saturation level (information related to the oxygen-saturation-level image 110). The information supporting the diagnosis of a physician or the like is, for example, an index value 102 (see FIG. 8) calculated by the index-value calculating unit 75.

By using an endoscope image acquired from the image acquiring unit 54 as the correction-value-calculation image, the correction-value calculating unit 72 calculates the correction value to be used for correcting the "endoscope image to be used during the main operation", the "biological information to be calculated during the main operation", or the "data to be used for calculation of biological information during the main operation". The target that is to be corrected by using the correction value calculated by the correction-value calculating unit 72 from among the "endoscope image to be used during the main operation", the "biological information to be calculated during the main operation", and the "data to be used for calculation of biological information during the main operation" depends on the actual embodiment of the special observation mode.

By using the correction value calculated by the correction-value calculating unit 72, the correction unit 73 corrects the "endoscope image to be used during the main operation", the "biological information to be calculated during the main operation", or the "data to be used for calculation of biological information during the main operation". As a matter of course, if the correction-value calculating unit 72 calculates the correction value targeting the "endoscope image to be used during the main operation", by using the correction value calculated by the correction-value calculating unit 72, the correction unit 73 corrects the "endoscope image to be used during the main operation". The same applies to a case of the "biological information to be calculated during the main operation" or the "data to be used for calculation of biological information during the main operation".

At least any one of the calculation of the correction value by the correction-value calculating unit 72 or the use of the correction value by the correction unit 73 (i.e., execution of correction) is performed in response to an input of an instruction from the input unit 74. The input unit 74 inputs, in accordance with the setting, an instruction for calculating the correction value (hereinafter this instruction will be referred to as a correction-value calculating instruction) or an instruction for executing correction of the "endoscope image to be used during the main operation", the "biological information to be calculated during the main operation", and the "data to be used for calculation of biological information during the main operation" (hereinafter this instruction will be referred to as a correction executing instruction) by using the correction value into the special processing unit 63. Accordingly, the timing of correction executed by the correction unit 73 by using the correction value is a case in which the correction-value calculating unit 72 calculates the correction value in response to the correction-value calculating instruction or a case in which the correction unit 73 obtains the correction executing instruction.

In a case of the setting in which the input unit 74 inputs the correction-value calculating instruction, the correction-value calculating unit 72 does not calculate the correction value until the correction-value calculating instruction is input from the input unit 74. Accordingly, until the correction-value calculating unit 72 calculates the correction value, the correction unit 73 does not execute correction. On the other hand, in a case in which the correction-value calculating instruction is input from the input unit 74 into the special processing unit 63, the correction-value calculating unit 72 calculates the correction value. Subsequently, the correction unit 73 automatically executes correction by using the correction value calculated by the correction-value calculating unit 72.

In a case of the setting in which the input unit 74 inputs the correction executing instruction, the correction unit 73 does not execute correction until the correction executing instruction is input from the input unit 74. Subsequently, when the correction executing instruction is input from the input unit 74, the correction unit 73 executes correction. In a case of the setting in which the input unit 74 inputs the correction executing instruction, the correction-value calculating unit 72 can calculate the correction value as appropriate even before the correction executing instruction is input from the input unit 74. In this case, the correction executing instruction is also an instruction for allowing use of the correction value that has been calculated. In addition, the correction-value calculating unit 72 may calculate the correction value when the correction executing instruction is input from the input unit 74.

The input unit 74 is an input screen (graphical user interface (GUI)) displayed on the monitor 18 or an operating unit included in the endoscope system 10. The "operating unit" included in the endoscope system 10 includes, in addition to the operating unit 12b forming a part of the endoscope 12, an operation device that is independent of the endoscope 12, such as a foot switch (not illustrated) or the console 19. In addition, the "operating unit" included in the endo scope system 10 also includes, not only the operation device connected to the endoscope 12, but also an operation device connected to the processor device 16 or the light source device 14. That is, the "operating unit" included in the endoscope system 10 directly or indirectly includes all operation devices by which the correction-value calculating instruction or the correction executing instruction can be input into the special processing unit 63. In this embodiment, the input unit 74 is a GUI and inputs the correction-value calculating instruction into the correction-value calculating unit 72.

The index-value calculating unit 75 calculates one or more types of index values 102 by using an endoscope image acquired from the image acquiring unit 54. The index value 102 is a numerical value used as a determination reference for determining whether the correction value is to be calculated or whether the correction value is to be used. Note that the index value 102 is substantially the same in a case in which the index value 102 is used as a determination reference for determining whether the correction value is to be calculated or a determination reference for determining whether the correction value is to be used. In a case of the setting in which the input unit 74 inputs a correction calculation instruction, the index value 102 is used as a determination reference for determining whether the correction value is to be calculated; in a case of the setting in which the input unit 74 inputs a correction executing instruction, the index value 102 is used as a determination reference for determining whether the correction value is to be used.

More specifically, the index-value calculating unit 75 calculates the index value 102 regarding any one or more of a movement amount of the observation target compared between endoscope images (hereinafter this amount will be referred to as an inter-image movement amount), a movement amount of the observation target in a single endoscope image (hereinafter this amount will be referred to as an intra-image movement amount), the brightness of the observation target or the endoscope image, the pixel value of the endoscope image, and the presence and absence or the amount of an attached matter.

The inter-image movement amount is, for example, the orientation or degree of movement, rotation, or deformation of the observation target when endoscope images acquired by the endoscope 12 at different timings, such as the B1 image and the B2 image, are compared with each other, or a complex numerical value that is obtained through computation using these. The orientation or degree of movement or the like is calculated for a corresponding point among a plurality of endoscope images. In a case in which the orientation or degree of movement or the like is calculated for a plurality of points, a statistic such as the average value, the median value, or the maximum value can be used as the movement amount. Note that the inter-image movement amount automatically includes information about, for example, the degree of movement of the observation target (relative movement of the observation target as a result of movement of the endoscope 12) as a result of a change in an image capturing position and a change in an image capturing angle.

The intra-image movement amount is a numerical value representing the level of blur of the endoscope image as a result of the movement, rotation, or deformation of the observation target at the time of capturing the endoscope image, and is, for example, a numerical value obtained by frequency analysis of the endoscope image. The intra-image movement amount automatically includes information about, for example, the degree of movement of the observation target (relative movement of the observation target as a result of movement of the endoscope 12) as a result of a change in an image capturing position and a change in an image capturing angle at the time of capturing the endoscope image.

The brightness of the observation target or the endoscope image is, for example, the luminance, brightness, or the like of the entire observation target or endoscope image or a specific part thereof (e.g., center part). The index-value calculating unit 75 calculates, for example, a statistic such as the average value or the median value of the luminance, brightness, or the like of pixels in the entire endoscope image or a specific part thereof, as the index value 102 regarding brightness.

The pixel value of the endoscope image is, for example, a statistic such as the average value, the median value, the maximum value, or the minimum value of pixel values of specific pixels or pixel values in a specific part of the endoscope image or the entire endoscope image. The index-value calculating unit 75 can calculate the appearance frequency of pixel values, the distribution of pixel values, or a statistic (e.g., standard deviation) regarding the distribution of pixel values in a specific part of the endoscope image or the entire endoscope image, as the index value 102 regarding the pixel value of the endoscope image.

The attached matter is, for example, residue, mucus, or medicine that has been sprayed (or applied, injected, or given without using the endoscope 12). The amount of the attached matter is the number, area, color, or density (coloring density due to the attached matter) of sections where the attached matter is present.

The index-value calculating unit 75 calculates the above index value 102 at least during the correction operation. Upon acquiring the index value 102 from the index-value calculating unit 75, the display control unit 66 causes the monitor 18 to display the observation image (the normal observation image 101 or the special observation image) side by side or in a superimposed manner. Thus, a physician or the like can understand the index value 102 calculated by the index-value calculating unit 75 in real time together with the observation image. Accordingly, by viewing the index value 102, it is possible to easily determine whether the conditions are appropriate for calculation of the correction value (i.e., whether the correction value is to be calculated) or whether the correction can be appropriately executed by using the correction value calculated by the correction-value calculating unit 72 (i.e., whether the correction value is to be used). If it is determined, on the basis of the index value 102, that the conditions are appropriate for calculation of the correction value or that the correction can be appropriately executed by using the correction value calculated by the correction-value calculating unit 72, the correction-value calculating instruction or the correction executing instruction is input into the special processing unit 63 by using the input unit 74, and accordingly, the correction value is calculated, or correction is executed.

Figure 4:
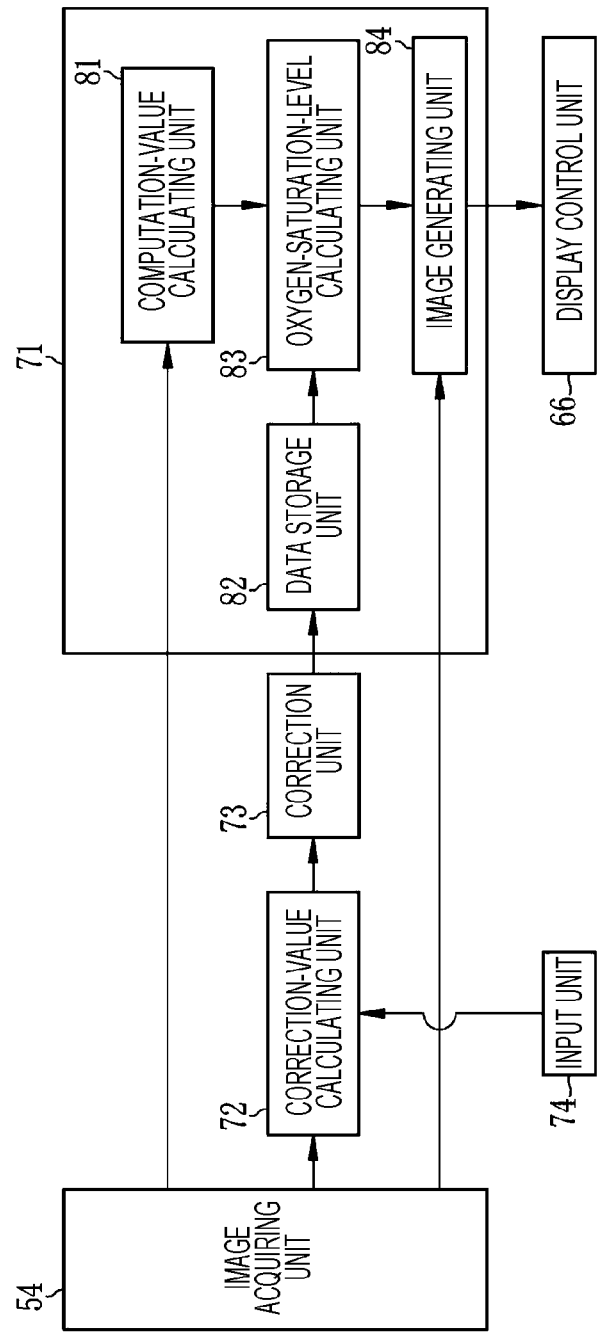
FIG. 4 is a block diagram of a special-observation-image generating unit in a first embodiment.

Since the special observation mode in this embodiment is the oxygen-saturation-level observation mode, as illustrated in FIG. 4, the special-observation-image generating unit 71 includes a computation-value calculating unit 81, a data storage unit 82, an oxygen-saturation-level calculating unit 83, and an image generating unit 84.

The computation-value calculating unit 81 acquires a plurality of endoscope images from the image acquiring unit 54, and by using the plurality of endoscope images, calculates computation values to be used by the oxygen-saturation-level calculating unit 83 for calculating the oxygen saturation level. Specifically, the computation-value calculating unit 81 acquires a B1 image, a B2 image, a G2 image, and an R2 image. Subsequently, the computation-value calculating unit 81 calculates a ratio B1/G2 of the B1 image to the G2 image and a ratio R2/G2 of the R2 image to the G2 image for each pixel. The ratio B1/G2 and the ratio R2/G2 are computation values to be used for calculating the oxygen saturation level.

Figure 5:
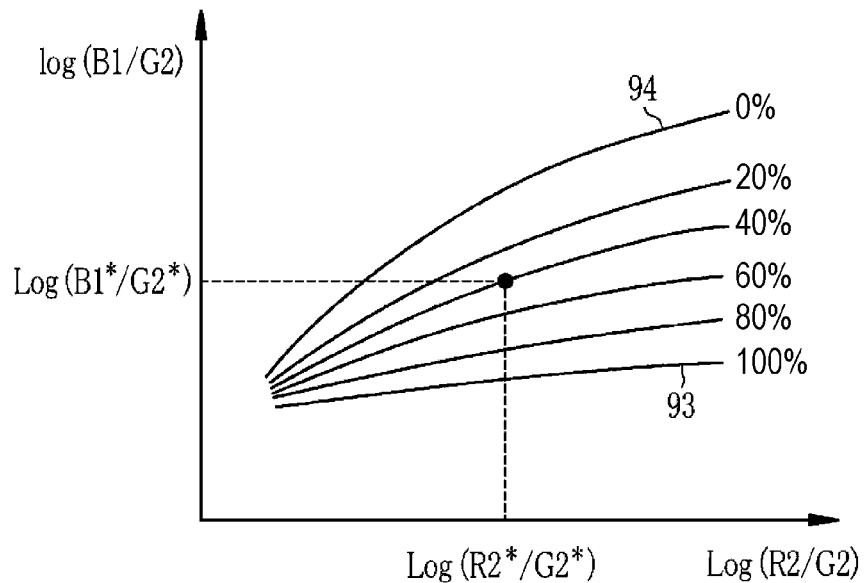
FIG. 5 illustrates a feature space representing a correlation between a computation value and an oxygen saturation level.

The data storage unit 82 stores data to be used by the oxygen-saturation-level calculating unit 83 for calculating the oxygen saturation level by using the above computation values calculated by the computation-value calculating unit 81. That is, the data storage unit 82 stores the correlation between the computation values and the oxygen saturation level in the form of, for example, an LUT. As illustrated in FIG. 5, when the correlation is represented in a feature space formed by using a vertical axis Log (B1/G2) and a horizontal axis Log (R2/G2), isopleths each connecting points of the same oxygen saturation level are formed in substantially the lateral direction. In addition, as the oxygen saturation level is higher, the isopleth is located lower in the vertical direction. For example, an isopleth 93 representing 100% oxygen saturation level is located below an isopleth 94 representing 0% oxygen saturation level.

Figure 6:
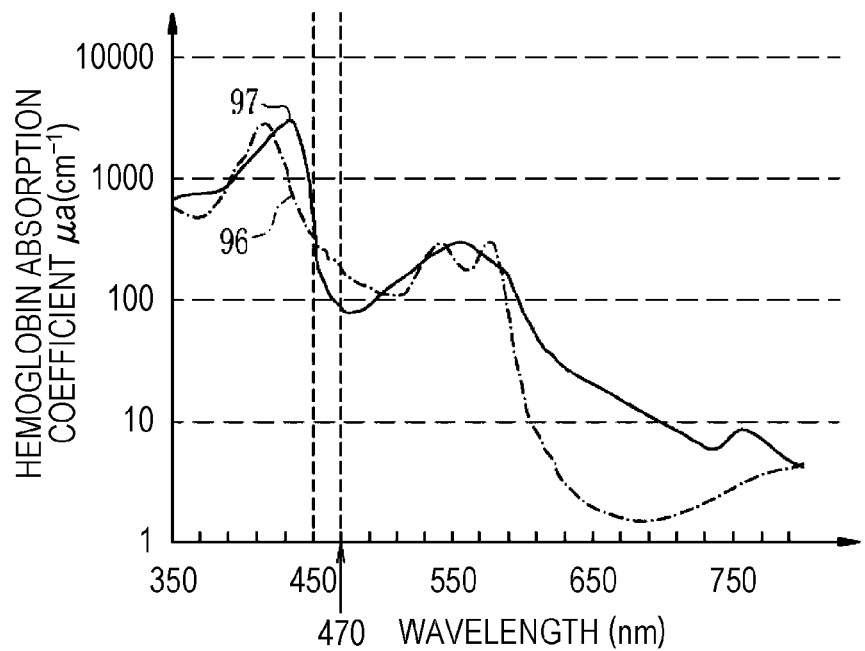
FIG. 6 is a graph illustrating absorption coefficients of oxyhemoglobin and deoxyhemoglobin.

The above correlation is closely related to absorption characteristics of oxyhemoglobin (graph 96) and deoxyhemoglobin (graph 97) illustrated in FIG. 6. Specifically, the wavelength (about 470±10 nm) of the second blue light BL has a large difference between the absorption characteristics of oxyhemoglobin and the absorption characteristics of deoxyhemoglobin. Thus, the absorption amount changes depending on the oxygen saturation level of hemoglobin. Accordingly, it is easy to handle the information about the oxygen saturation level by using the second blue light BL. Therefore, the oxygen saturation level can be calculated by using the ratio B 1/G2 for standardizing the B1 image by using the G2 image for correcting uneven illuminance or the like. However, the ratio B1/G2 is dependent on, not only the oxygen saturation level, but also the blood volume. Therefore, in addition to the ratio B1/G2, by using the ratio R2/G2 that changes mainly depending on the blood volume, the oxygen saturation level can be calculated regardless of the blood volume. Note that the wavelength (about 540±20 nm) of the green light G included in the G2 image has a relatively high hemoglobin absorption coefficient, and thus, the absorption coefficient easily changes depending on the blood volume.

Note that the position and shape of isopleths in the above feature space are obtained in advance as a result of a physical simulation of light scattering. In addition, although the data storage unit 82 stores the correlation between the ratio B1/G2 and the oxygen saturation level and the correlation between the ratio R2/G2 and the oxygen saturation level, the data storage unit 82 can store other correlations. For example, in a case in which the oxygen saturation level is calculated by using computation values obtained as results of other computations (e.g., difference processing) that are different from the above computation based on the B1 image, the B2 image, the G2 image, and the R2 image (hereinafter, these values will be referred to as other computation values), the data storage unit 82 can store the correlation for associating the other computation values with the oxygen saturation level.

By using the above correlation, which is data stored in the data storage unit 82, and the computation values calculated by the computation-value calculating unit 81, the oxygen-saturation-level calculating unit 83 calculates the oxygen saturation level. Specifically, referring to the correlation stored in the data storage unit 82, the oxygen-saturation-level calculating unit 83 calculates the oxygen saturation level corresponding to the ratio B1/G2 and the ratio R2/G2 for each pixel. For example, referring to the correlation stored in the data storage unit 82, the oxygen saturation level corresponding to the ratio B1/G2 and the ratio R2/G2 for a certain pixel is "40%". Accordingly, the oxygen-saturation-level calculating unit 83 calculates the oxygen saturation level in this pixel as "40%" (see FIG. 5). In a case in which the correlation stored in the data storage unit 82 is corrected by the correction unit 73, the oxygen-saturation-level calculating unit 83 calculates the oxygen saturation level referring to the corrected correlation.

Note that the ratio B1/G2 and the ratio R2/G2 are unlikely to become extremely high or extremely low. That is, the combination of values of the ratio B1/G2 and the ratio R2/G2 is unlikely to be distributed below the isopleth 93 (see FIG. 5), which is the upper limit of the 100% oxygen saturation level, or, in contrast, above the isopleth 94 (see FIG. 5), which is the lower limit of the 0% oxygen saturation level. If, by any possibility, the combination of values of the ratio B1/G2 and the ratio R2/G2 is distributed below the isopleth 93, which is the upper limit, the oxygen-saturation-level calculating unit 83 calculates the oxygen saturation level of the pixel as "100%", which is the upper limit. Similarly, if the combination of values of the ratio B1/G2 and the ratio R2/G2 is distributed above the isopleth 93, which is the lower limit, the oxygen-saturation-level calculating unit 83 calculates the oxygen saturation level of the pixel as "0%". In addition, if points corresponding to the ratio B1/G2 and the ratio R2/G2 are not distributed between the upper limit isopleth 93 and the lower limit isopleth 94, the low reliability of the oxygen saturation level in this pixel may be displayed, or the oxygen saturation level may not be calculated.

During the main operation, by using the plurality of endoscope images acquired from the image acquiring unit 54 and the oxygen saturation level calculated by the oxygen-saturation-level calculating unit 83, the image generating unit 84 generates the oxygen-saturation-level image 110. More specifically, the image generating unit 84 acquires the B2 image, the G2 image and the R2 image and multiplies the endoscope images by gains in accordance with the oxygen saturation level pixel by pixel. For example, for a pixel in which the oxygen saturation level is 60% or more, the image generating unit 84 multiplies each of the B2 image, the G2 image, and the R2 image by the gain "1". In contrast, for a pixel in which the oxygen saturation level is less than 60%, the image generating unit 84 multiplies the B2 image by a gain less than "1" and multiplies the G2 image and the R2 image by a gain greater than or equal to "1". Subsequently, the image generating unit 84 generates a color observation image by using the B2 image, the G2 image, and the R2 image multiplied by the gains as described above. The observation image generated by using the B2 image, the G2 image, and the R2 image multiplied by the gains in accordance with the oxygen saturation level pixel by pixel in the above manner is the oxygen-saturation-level image 110. The image generating unit 84 causes the monitor 18 to sequentially display the generated oxygen-saturation-level image 110 via the display control unit 66.

In the oxygen-saturation-level image 110 generated by the image generating unit 84, a high-oxygen region (region where the oxygen saturation level is 60% or more and 100% or less in this embodiment) has natural colors as in the normal observation image 101. On the other hand, in a low-oxygen region (region where the oxygen saturation level is 0% or more and less than 60% in this embodiment)

where the oxygen saturation level is below a specific value, in accordance with the calculated oxygen saturation level, coloring is provided by using pseudo colors that are different from the colors of the normal observation image 101. Note that, although the image generating unit 84 multiplies the gains for providing pseudo colors in only the low-oxygen region in a case of the oxygen-saturation-level observation mode in this embodiment, also in the high-oxygen region, gains in accordance with the oxygen saturation level may be multiplied so as to provide pseudo colors in the entire oxygen-saturation-level image 110. In addition, although the boundary between the low-oxygen region and the high-oxygen region is the oxygen saturation level being 60%, the oxygen saturation level as the boundary may be set to any value.

While the oxygen-saturation-level image 110 is generated as described above during the main operation, the image generating unit 84 generates the normal observation image 101 during the correction operation. Specifically, during the correction operation, the image generating unit 84 acquires the B2 image, the G2 image, and the R2 image from the image acquiring unit 54, and generates a color observation image by using these endoscope images. This observation image generated by using the B2 image, the G2 image, and the R2 image acquired from the image acquiring unit 54 without any change in this manner is the normal observation image 101 in the oxygen-saturation-level observation mode. That is, in the normal observation image 101 generated by the image generating unit 84, in almost the same manner as the normal observation image generated by the normal processing unit 62 in the normal observation mode, the observation target is represented by using natural colors. The image generating unit 84 causes the monitor 18 to sequentially display the normal observation image 101 generated during the correction operation via the display control unit 66.

During the correction operation in this embodiment, the input unit 74 is a GUI, by which the correction-value calculating instruction is input into the correction-value calculating unit 72. In addition, the correction unit 73 corrects the correlation (data to be used for calculation of the oxygen saturation level) stored in the data storage unit 82. Accordingly, the correction-value calculating unit 72 calculates the correction value for correcting the correlation between the computation value and the oxygen saturation level.

Specifically, the correction-value calculating unit 72 acquires the B1 image, the B2 image, the G2 image, and the R2 image from the image acquiring unit 54. Subsequently, by using the plurality of endoscope images, the ratio B1/G2 of the B1 image to the G2 image and the ratio R2/G2 of the R2 image to the G2 image are calculated pixel by pixel. That is, the correction-value calculating unit 72 calculates substantially the same computation values as those of the computation-value calculating unit 81. Subsequently, by using the calculated computation values and the correlation that is stored in advance in the data storage unit 82 and is not subjected to correction (hereinafter this correlation will be referred to as default correlation), the oxygen saturation level is calculated pixel by pixel as in the oxygen-saturation-level calculating unit 83, and its representative value is obtained. The representative value is the average value in this embodiment, but can be another statistic such as the median value or the mode value.

If the plurality of endoscope images acquired by the correction-value calculating unit 72 are images of the observation target captured under conditions that are appropriate for calculating the correction value, the representative value is substantially a fixed value. For example, if images of an appropriate portion without an obvious lesion are captured for the correction operation and image capturing conditions are appropriate, the representative value of the oxygen saturation level is a specific value (e.g., about 70%, depending on the observed part). In addition, the shape and correlation of each isopleth in a feature space is substantially fixed regardless of the individual difference or the like of the observation target. Accordingly, when the representative value of the oxygen saturation level calculated by the correction-value calculating unit 72 is compared with this specific value, it is possible to obtain the degree of shift of the default correlation in the feature space so as to accurately calculate the oxygen saturation level of the observation target. The shift amount and shift direction of the default correlation are the correction amounts calculated by the correction-value calculating unit 72.

In accordance with the shift amount and shift direction calculated by the correction-value calculating unit 72, the correction unit 73 corrects the default correlation. In addition, during the main operation, the oxygen-saturation-level calculating unit 83 calculates the oxygen saturation level by using the corrected correlation.

Figure 7:
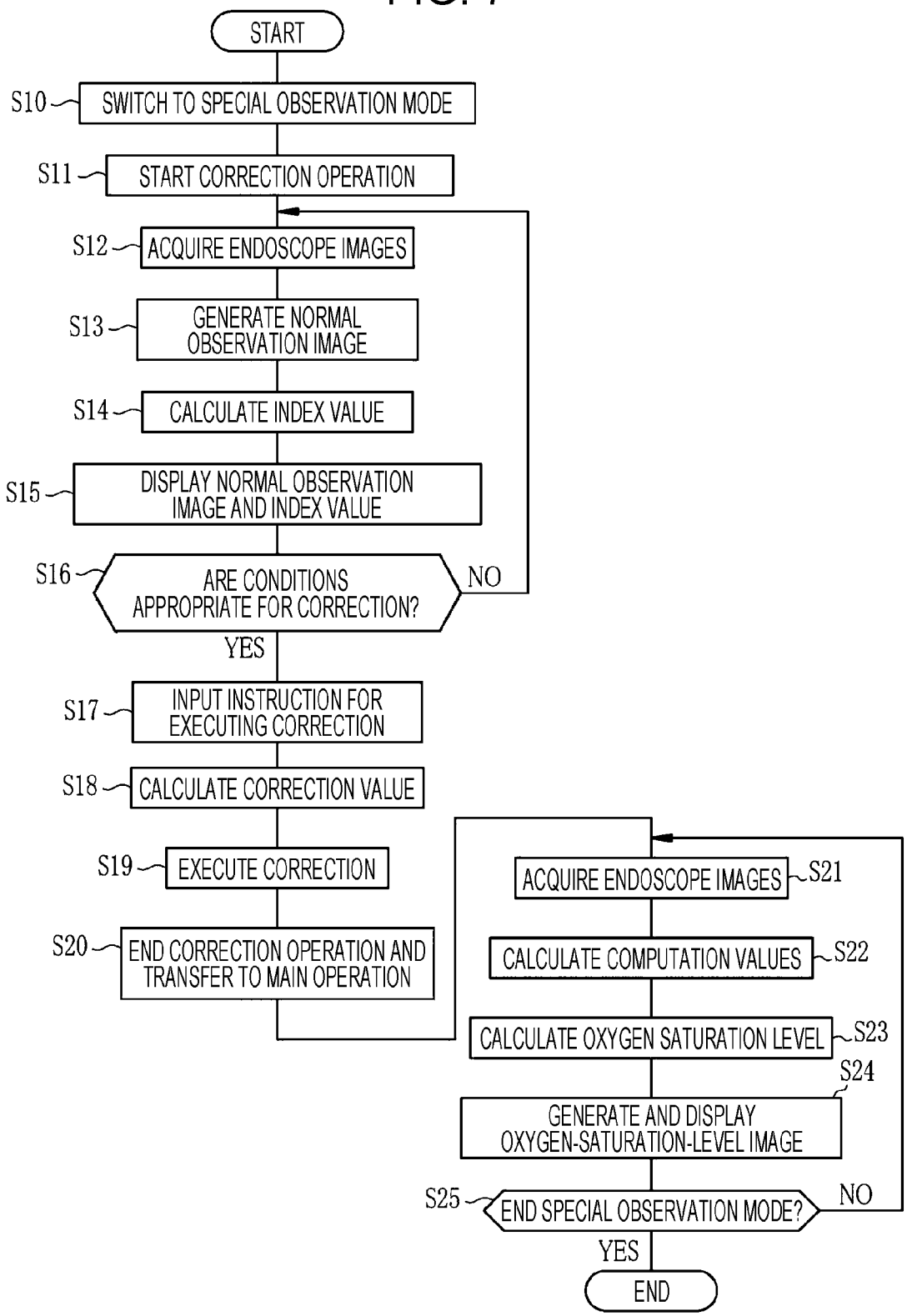
FIG. 7 is a flowchart of a special observation mode (oxygen-saturation-level observation mode)
Figure 8:
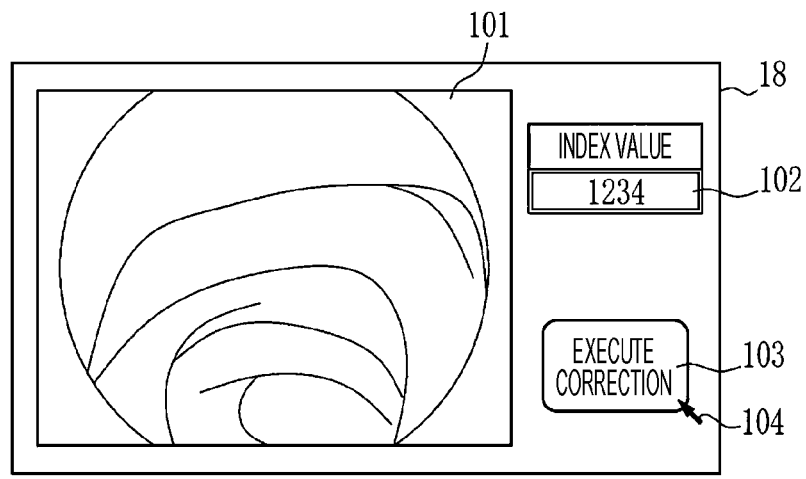
FIG. 8 illustrates a display screen of a monitor displaying an index value.

Next, an operation flow in the oxygen-saturation-level observation mode, which is the special observation mode in this embodiment, will be described with reference to the flowchart in FIG. 7. First, the mode switch 13*a* is operated to switch the observation mode to the oxygen-saturation-level observation mode (S10), and the special processing unit 63 starts the correction operation (S11). Upon start of the correction operation, the image acquiring unit 54 sequentially acquires a plurality of endoscope images (S12). Subsequently, the special-observation-image generating unit 71 generates the normal observation image 101 in the image generating unit 84 (S13). On the other hand, by using the plurality of endoscope images acquired from the image acquiring unit 54, the index-value calculating unit 75 calculates the index value 102 (S14). Accordingly, the display control unit 66 acquires the normal observation image 101 from the image generating unit 84 and acquires the index value 102 from the index-value calculating unit 75 to cause the monitor 18 to display these (S15). For example, as illustrated in FIG. 8, the display control unit 66 causes the monitor 18 to display the index value 102 beside the normal observation image 101. In addition, the display control unit 66 also causes the monitor 18 to display a correction execution button 103, which is a GUI for inputting a correction executing instruction. In this embodiment, the correction execution button 103 is the input unit 74.

When the monitor 18 displays the normal observation image 101 and the index value 102 during the correction operation as described above, a physician or the like views the normal observation image 101 and the index value 102 to determine whether the conditions are appropriate for correction, that is, whether an image of an appropriate portion without an obvious lesion is captured and the image capturing conditions are appropriate (S16). A physician or the like can determine whether an image of an appropriate portion without an obvious lesion is captured by viewing the normal observation image 101. Also, a physician or the like can determine whether the image capturing conditions are appropriate for correction by viewing the normal observation image 101. However, since the monitor 18 displays the index value 102 that supports this determination, a physician or the like can more reliably determine whether the image capturing conditions are appropriate on the basis of the index value 102.

If a physician or the like determines that the conditions are not appropriate for correction by viewing the normal observation image 101 and the index value 102, they do not press the correction execution button 103. Accordingly, the endoscope system 10 repeatedly performs step S12 to step S15 (S16: NO), and the normal observation image 101 and the index value 102 are sequentially updated. In this case, a physician or the like adjusts the image capturing position or the like so as to set conditions that are appropriate for correction while observing the normal observation image 101 and the index value 102 being updated.

On the other hand, if it is determined that the conditions are appropriate for correction by viewing the normal observation image 101 and the index value 102 (S16: YES), a physician or the like operates a pointer 104 (see FIG. 8) by using the console 19 and inputs a correction-value calculating instruction into the correction-value calculating unit 72 by pressing the correction execution button 103 serving as the input unit 74 (S17). In response to the input of the correction-value calculating instruction, the correction-value calculating unit 72 calculates the correction value by using the plurality of endoscope images acquired from the image acquiring unit 54 (S18). Subsequently, by using the correction value calculated by the correction-value calculating unit 72, the correction unit 73 corrects the correlation stored in the data storage unit 82 (S19). Subsequently, the control unit 52 ends the correction operation in the oxygen-saturation-level observation mode and transfers to the main operation (S20).

Figure 9:
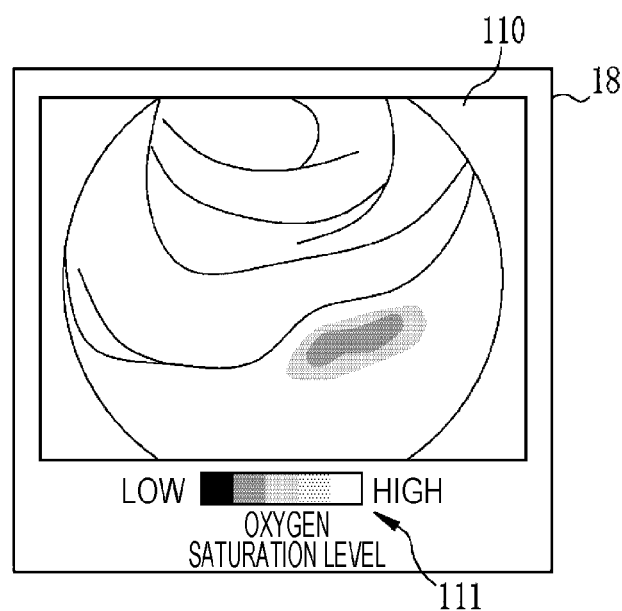
FIG. 9 illustrates a display screen of a monitor displaying an oxygen-saturation-level image.

Upon transfer to the main operation, the special-observation-image generating unit 71 acquires a plurality of endoscope images again from the image acquiring unit 54 (S21), and by using the plurality of endoscope images, the computation-value calculating unit 81 calculates computation values (S22). Subsequently, by using the computation values and the corrected correlation that is corrected by the correction unit 73 in accordance with the data storage unit 82, the oxygen-saturation-level calculating unit 83 calculates the oxygen saturation level pixel by pixel (S23). Upon the oxygen saturation level being calculated by the oxygen-saturation-level calculating unit 83, by using the oxygen saturation level calculated by the oxygen-saturation-level calculating unit 83 and the plurality of endoscope images, the image generating unit 84 generates the oxygen-saturation-level image 110 (see FIG. 9), and, as illustrated in FIG. 9, the oxygen-saturation-level image 110 is displayed on the monitor 18 via the display control unit 66 (S24). At this time, the display control unit 66 causes an indicator 111 to be displayed beside the oxygen-saturation-level image 110, the indicator 111 indicating the relationship between the color of the oxygen-saturation-level image 110 and the oxygen saturation level. The steps (S21 to S24) of the main operation are repeatedly performed until the end of the special observation mode (S25).

As described above, the endoscope system 10 calculates the index value 102 during the correction operation in the special observation mode and causes the monitor 18 to display the index value 102 to support determination. Accordingly, it is possible to easily determine whether the image capturing conditions are appropriate for acquiring a correction-value-calculation image and for executing correction during the correction operation. In particular, even in a case in which it is difficult for a physician or the like to determine whether the image capturing conditions are appropriate for acquiring a correction-value-calculation image and for executing correction by only viewing the normal observation image 101, they can easily perform determination by viewing the index value 102. Accordingly, with the endoscope system 10, it is more unlikely to end up in failure of calculation of the correction value and correction of the correlation or the like than with an endoscope system of the related art. In addition, the oxygen-saturation-level image 110 that is displayed on the monitor 18 during the main operation indicates an accurate value regardless of the individual difference or the like of the observation target because the oxygen saturation level has been calculated by the oxygen-saturation-level calculating unit 83 by using the corrected correlation.

Figure 10:
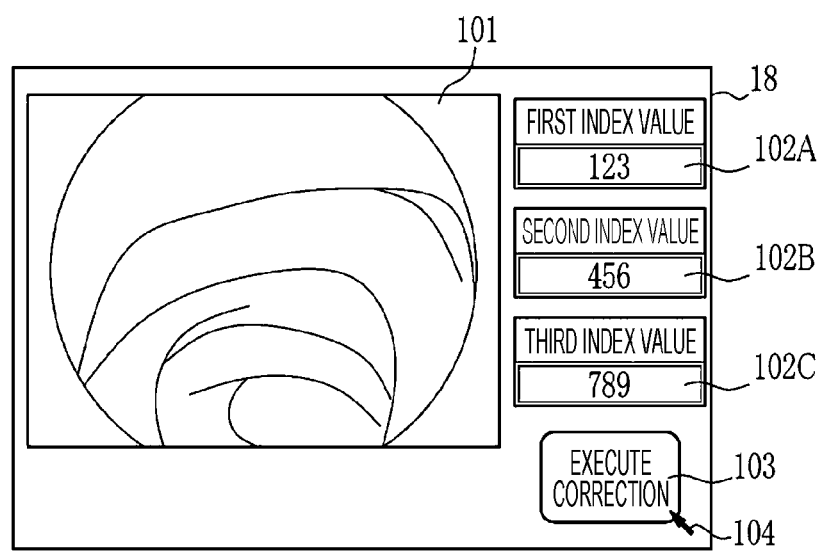
FIG. 10 illustrates a display screen of a monitor displaying a plurality of types of index values.

In the above first embodiment, the index-value calculating unit 75 calculates the single index value 102 and causes the monitor 18 to display the single index value 102 (see FIG. 8). However, the index-value calculating unit 75 preferably calculates a plurality of types of the index values 102 such as a first index value 102A, a second index value 102B, and a third index value 102C as illustrated in FIG. 10 and preferably causes the monitor 18 to display the first index value 102A, the second index value 102B, and the third index value 102C. Accordingly, it is possible to determine whether the image capturing conditions are appropriate for acquiring a correction-value-calculation image and for executing correction from a plurality of aspects, and as a result, it is possible to more reliably calculate an accurate oxygen saturation level. Note that the first index value 102A, the second index value 102B, and the third index value 102C are any of an inter-image movement amount, an intra-image movement amount, the brightness of the observation target or the endoscope image, the pixel value of the endoscope image, and the presence and absence or the amount of an attached matter. Although the three index values, which are the first index value 102A, the second index value 102B, and the third index value 102C, are calculated and displayed in FIG. 10, all of them or any two of them may be calculated and displayed as the index values 102.

In the above first embodiment, the correction unit 73 corrects the correlation, which is the "data to be used for calculation of biological information during the main operation". However, the correction unit 73 can correct the "endoscope image to be used during the main operation" or the "biological information to be calculated during the main operation".

Figure 11:
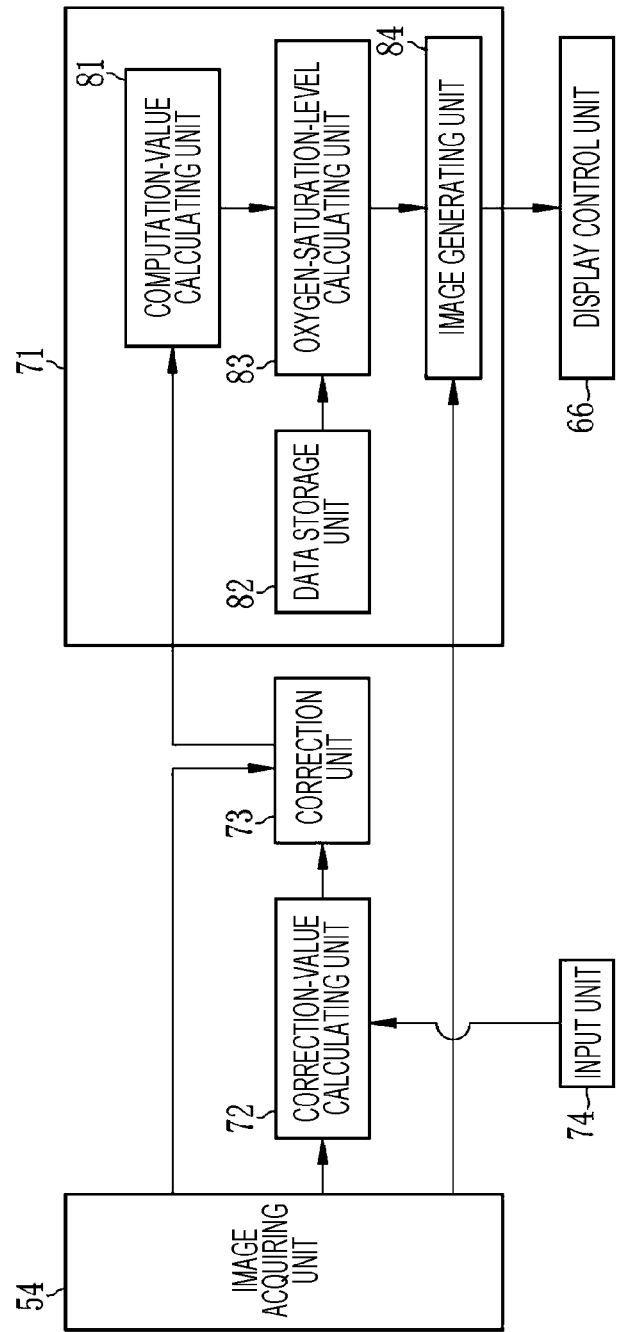
FIG. 11 is a block diagram of a special-observation-image generating unit in a modification example.

In a case in which the correction unit 73 corrects the "endoscope image to be used during the main operation", as illustrated in FIG. 11, the correction unit 73 acquires, from the image acquiring unit 54, an endoscope image to be used by the computation-value calculating unit 81 during the main operation. Subsequently, the corrected endoscope image is input into the computation-value calculating unit 81. Thus, as in the first embodiment, the accurate oxygen saturation level can be calculated. Note that the correction-value calculating unit 72 in this case calculates, for example, gains to be used for multiplication of one or more of the B1 image, the G2 image, and the R2 image such that the representative value of the oxygen saturation level becomes a specific value (e.g., 70%) when the default correlation is referred to and inputs the gains as correction values into the correction unit 73.

Figure 12:
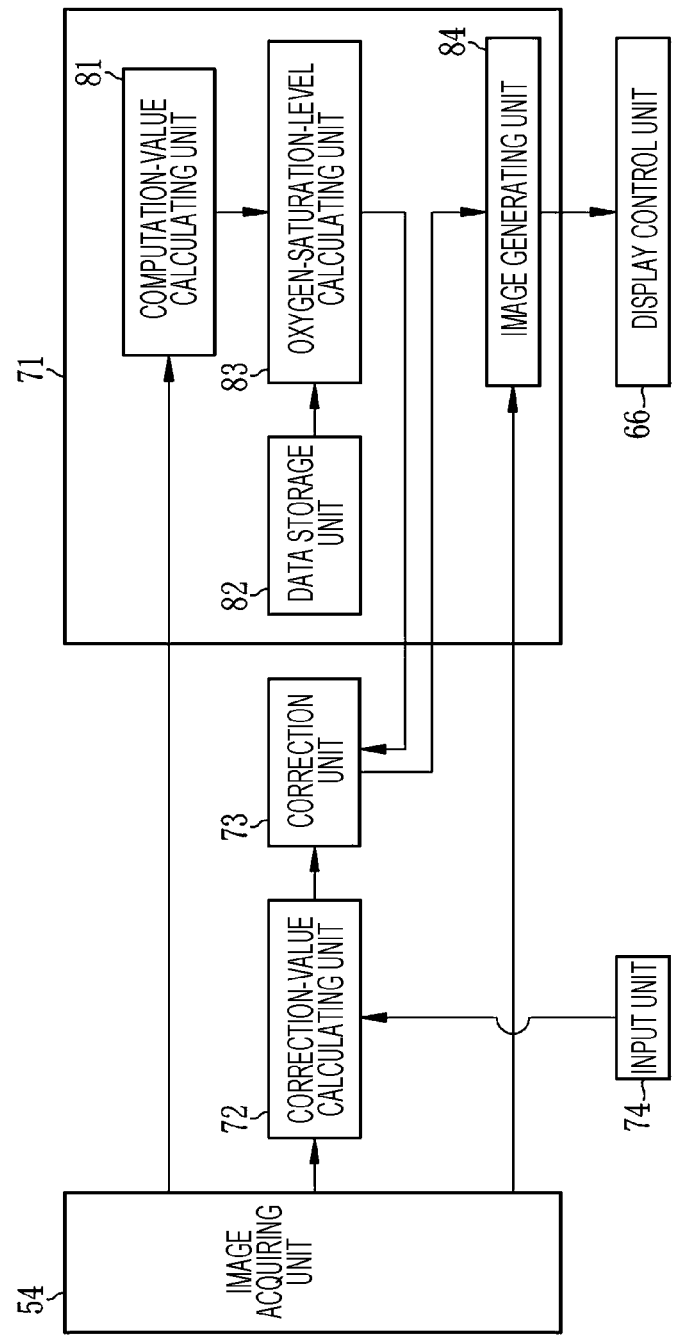
FIG. 12 is a block diagram of the special-observation-image generating unit in a modification example.

In addition, in a case in which the correction unit 73 corrects the "biological information to be calculated during the main operation", as illustrated in FIG. 12, the correction unit 73 acquires the oxygen saturation level calculated by the oxygen-saturation-level calculating unit 83. Subsequently, the corrected oxygen saturation level is input into the image generating unit 84. Thus, as in the first embodiment, the oxygen-saturation-level image 110 indicating the accurate oxygen saturation level can be generated and displayed. Note that the correction-value calculating unit 72 in this case calculates, for example, the representative value of the oxygen saturation level and a difference from a specific value (e.g., 70%) or the like as the correction value as in the above first embodiment. By performing addition, subtraction, multiplication, division, and the like on the oxygen saturation level calculated by the oxygen-saturation-level calculating unit 83 by using the correction value, the correction unit 73 can correct the oxygen saturation level to the accurate value.

Second Embodiment

Although the index value 102 is displayed on the monitor 18 in the first embodiment, it is preferable to further display "OK (allowed)" or "NG (not allowed)" as to whether the index value 102 is to be used for calculation of the correction value or whether the correction value is to be used. In this case, it is easy to understand the indication of the numerical value of the index value 102 without considering it. Thus, it is possible to more effectively support the determination as to whether the image capturing conditions are appropriate for correction.

Figure 13:
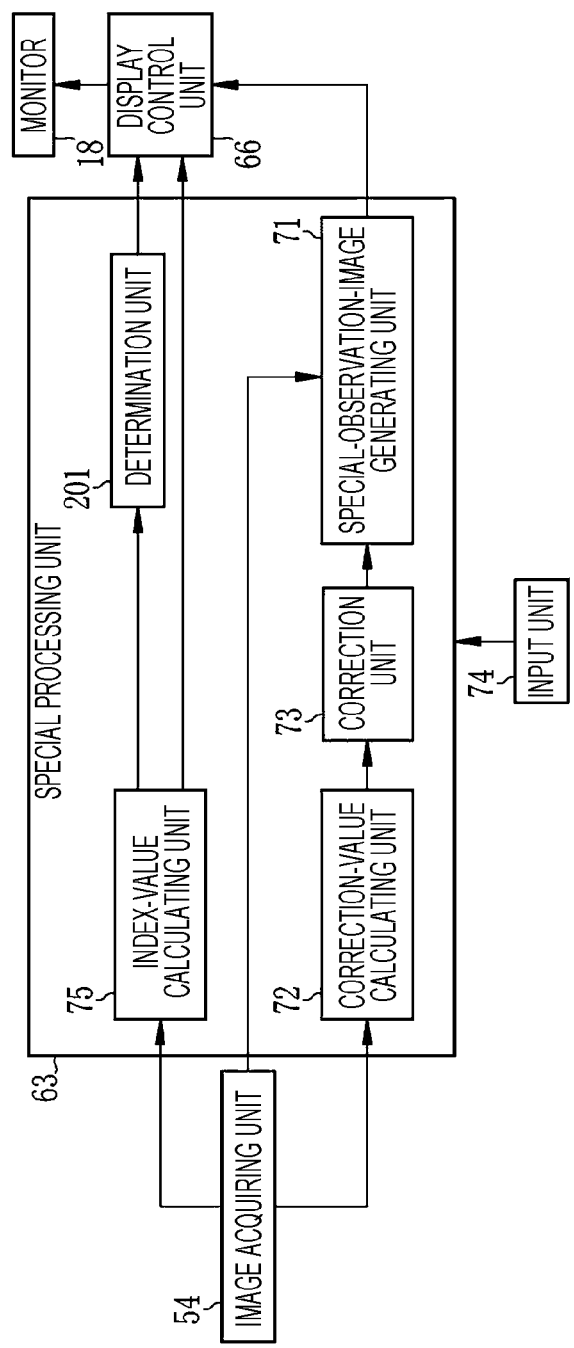
FIG. 13 is a block diagram of a special processing unit in a second embodiment.

In this case, as illustrated in FIG. 13, the special processing unit 63 is provided with a determination unit 201. The determination unit 201 acquires the index value 102 from the index-value calculating unit 75 to determine whether the correction value is to be calculated or whether the correction value is to be used (whether correction is to be executed). Specifically, the determination unit 201 compares the index value 102 with a threshold that has been determined in advance in accordance with the type of the index value 102. For example, if the index value 102 falls within a range defined by the threshold, the determination unit 201 determines that the index value 102 is to be used for calculation of the correction value or that the correction value is to be used ("OK"). On the other hand, if the index value 102 falls out of the range defined by the threshold, the determination unit 201 determines that the index value 102 is not to be used for calculation of the correction value or that the correction value is not to be used ("NG").

Figure 14:
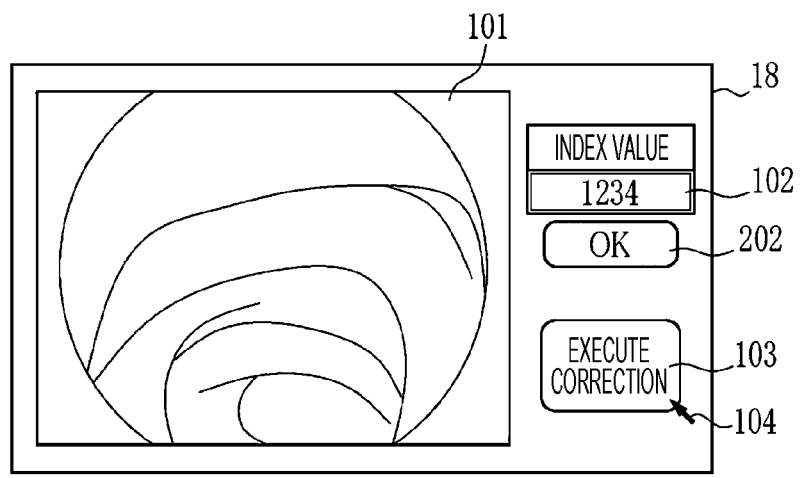
FIG. 14 illustrates a display screen of a monitor displaying a result of determination.

Subsequently, the determination unit 201 inputs the above determination result 202 (see FIG. 14) of "OK" or "NG" into the display control unit 66. Accordingly, as illustrated in FIG. 14, the display control unit 66 causes the determination result 202 ("OK" in FIG. 14) to be displayed in addition to the index value 102. While a physician or the like can determine whether the conditions are appropriate for correction by viewing the index value 102, the determination result 202 can make the determination more reliable and easier.

Note that the determination result 202 of the determination unit 201 has the same indication as the index value 102 in terms of a determination reference for determining whether the conditions are appropriate for correction, and thus, the determination result 202 is a type of the index value 102 having a different display mode. Accordingly, although both the index value 102 and the determination result 202 are displayed on the monitor 18 in FIG. 14, only the determination result 202 may be displayed as the index value 102 in the first embodiment. The case in which the index value 102 is displayed herein includes a case in which only the index value 102 is displayed, a case in which only the determination result 202 is displayed, and a case in which both the index value 102 and the determination result 202 are displayed, except for a case in which the index value 102 and the determination result 202 have to be distinguished from each other as in a case in which the index value 102 and the determination result 202 are displayed side by side as illustrated in FIG. 14.

Figure 15:
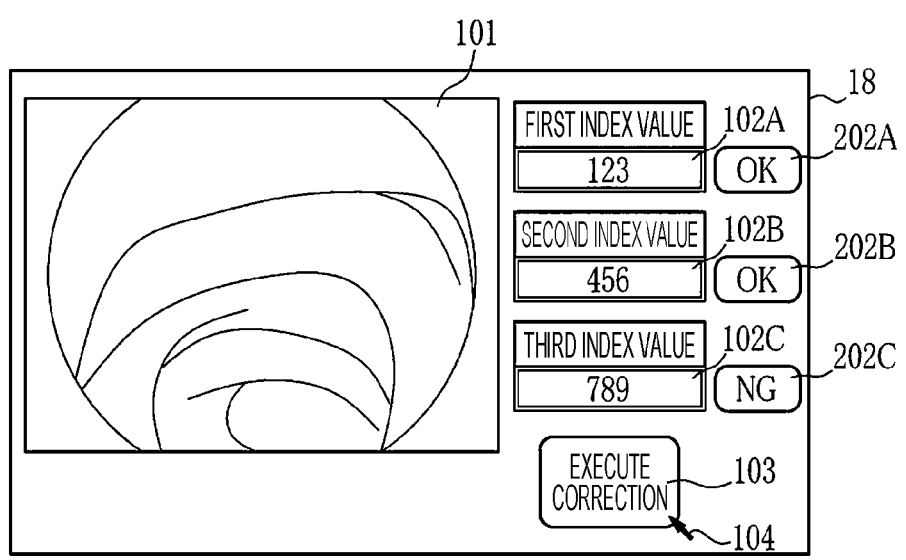
FIG. 15 illustrates a display screen of a monitor displaying a result of determination for each index value.

In a case in which a plurality of types of the index values 102 are calculated and displayed in the second embodiment, the determination unit 201 determines whether the correction value is to be calculated or the correction value is to be used for each of the index values 102. Subsequently, the determination result 202 for each of the index values 102 is displayed on the monitor 18. For example, as illustrated in FIG. 15, in a case in which the three index values 102, which are the first index value 102A, the second index value 102B, and the third index value 102C, are calculated and displayed, a determination result 202A for the first index value 102A, a determination result 202B for the second index value 102B, and a determination result 202C for the third index value 102C are each displayed on the monitor 18. In this case, it is possible to identify the index value 102 that causes NG determination if any of the determination results 202A, 202B, and 202C is "NG" that indicates inappropriate conditions for correction. Thus, it is possible to quickly understand what kind of image capturing conditions is to be improved. Accordingly, even when the conditions are not appropriate for correction, a physician or the like can appropriately and effectively adjust the image capturing conditions following a fixed guiding principle to quickly set conditions that are appropriate for correction, without unnecessarily changing the conditions such as the image capturing position.

Note that the threshold that is used for determination may differ for each of the index values 102. In addition, although the determination result 202 is displayed as a message of "OK" or "NG" in the second embodiment, the determination result 202 may be displayed by the turning on or off of an indicator, a character, a figure, an icon, a lamp, or the like (including display on the monitor 18 imitating a lamp or the like). For example, the determination result 202 can be indicated by using a lamp that is lit in red if the determination result 202 is "NG" and is lit in green if the determination result 202 is "OK". In a case in which the determination result 202 is displayed by using an indicator, levels may be provided for the threshold to be used for the determination of the determination unit 201, and the level to which the determination result 202 belongs may be displayed. For example, in a case in which the determination result 202 is displayed by using an indicator, the determination result 202 can be displayed in a plurality of levels by using different colors, different lengths of gauges, or the like depending on the determination result 202 being poor, fair, good, excellent, and the like so as to be visually understood in particular with ease.

Third Embodiment

Although the index value 102 and the determination result 202 are displayed on the monitor 18 in the second embodiment, if the determination result 202 is "NG", in accordance with the type of the index value 102 by which the determination result 202 becomes "NG", it is preferable to further display an improvement instruction 302 (see FIG. 17) regarding the image capturing conditions for endoscope images. With the improvement instruction 302, the image capturing conditions can be more appropriately and effectively adjusted so as to quickly set conditions that are appropriate for correction.

Figure 16:
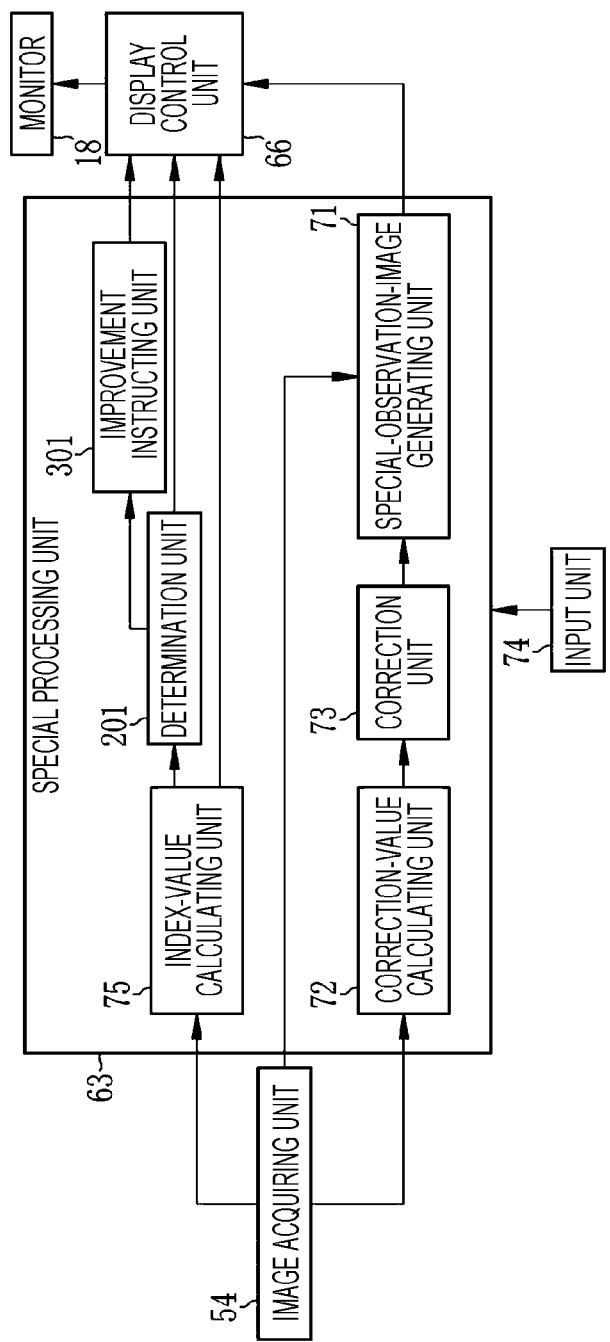
FIG. 16 is a block diagram of a special processing unit in a third embodiment.

In this case, as illustrated in FIG. 16, the special processing unit 63 is provided with an improvement instructing unit 301 in addition to the determination unit 201. The improvement instructing unit 301 acquires the index value 102 and the determination result 202 from the determination unit 201. Subsequently, if the determination result 202 is "NG", on the basis of the type of the index value 102 by which the determination result 202 becomes "NG" and the relationship with the threshold used by the determination unit 201, the improvement instructing unit 301 causes the monitor 18 to display the improvement instruction 302. The improvement instruction 302 is an instruction regarding the image capturing conditions for endoscope images and is, for example, a message indicating a guide principle for changing the determination result 202 from "NG" to "OK".

Figure 17:
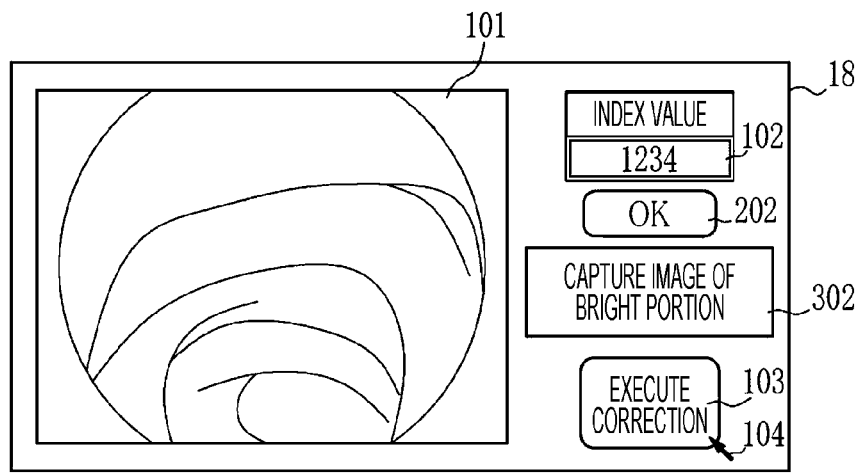
FIG. 17 illustrates a display screen of a monitor displaying an improvement instruction.

For example, as illustrated in FIG. 17, in a case in which the index value 102 is related to the brightness and the determination result 202 of the determination unit 201 is "NG", when the NG determination is due to an endoscope image being too dark in the relationship between the index value 102 and the threshold used by the determination unit 201, the improvement instructing unit 301 causes the monitor 18 to display the improvement instruction 302 indicating, "capture an image of a bright portion". In contrast, when the NG determination is due to an endoscope image being too bright, the improvement instructing unit 301 causes the monitor 18 to display the improvement instruction 302 indicating, "capture an image of a dark portion".

Besides, in a case in which the index value 102 is related to the inter-image movement amount or the intra-image movement amount and the determination result 202 of the determination unit 201 is "NG", when the NG determination is due to the movement of the observation target or the endoscope 12 being too large in the relationship between the index value 102 and the threshold used by the determination unit 201, the improvement instructing unit 301 causes the monitor 18 to display the improvement instruction 302 indicating, "capture an image with less movement". In a similar manner, in a case in which the index value 102 is related to the presence and absence or the amount of the attached matter and the determination result 202 of the determination unit 201 is "NG", the improvement instructing unit 301 causes the monitor 18 to display the improvement instruction 302 indicating, "clean the observation target" to remove the attached matter. In addition, if the image capturing distance is too short, the center portion of an endoscope image becomes dark. Accordingly, in a case in which the index value 102 is related to the brightness of the center portion of the endoscope image and the determination result 202 of the determination unit 201 is "NG", the improvement instructing unit 301 causes the monitor 18 to display the improvement instruction 302 indicating, for example, "have a greater image capturing distance" to promote adjustment of the image capturing distance. Note that, in a case in which a plurality of types of the index values 102 are calculated and determination is performed for each of the index value 102, similarly, the improvement instruction 302 is displayed for each of the index values 102 and the determination results 202.

Figure 18:
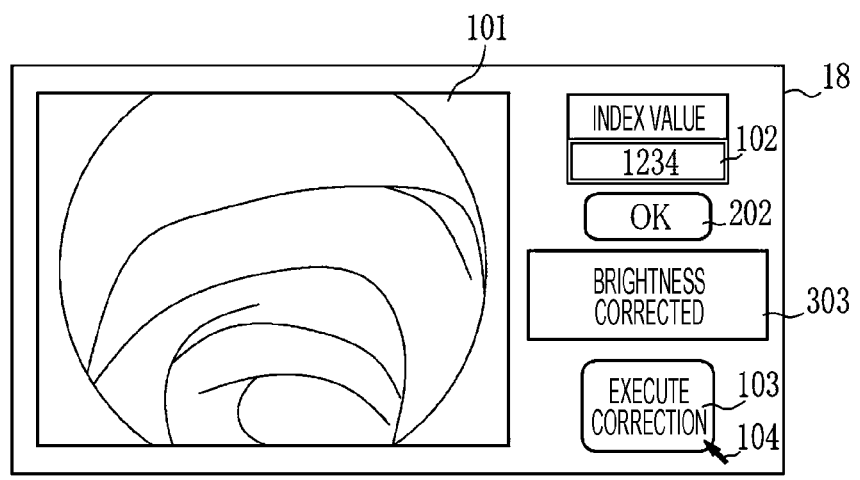
FIG. 18 illustrates a display screen of a monitor displaying a result of improvement determination.

After the monitor 18 has displayed the improvement instruction 302, it is preferable that the improvement instructing unit 301 further perform improvement determination for determining whether the image capturing conditions regarding the index value 102 by which the determination result 202 has been "NG" are improved and cause the monitor 18 to display the result of this improvement determination. For example, a result 303 of improvement determination is displayed as a message or the like as illustrated in FIG. 18. The improvement determination is performed by, for example, acquiring an endoscope image, or the index value 102 and the determination result 202.

Note that the same plurality of endo scope images are acquired during the main operation and the correction operation in the above first to third embodiments. However, the endoscope system 10 can acquire different plurality of endoscope images during the main operation and the correction operation and can perform each of the main operation and the correction operation.

Specifically, in the above first to third embodiments, the image acquiring unit 54 acquires the same endoscope image during the correction operation and the main operation, which is the correction-value-calculation image and is a biological-information-calculation image. Accordingly, during the correction operation, the correction-value calculating unit 72 calculates the correction value by using the biological-information-calculation image, and the index-value calculating unit 75 calculates the index value 102 by using the biological-information-calculation image that is used by the correction-value calculating unit 72 to calculate the correction value.

On the other hand, depending on the content of the special observation mode, for example, the endoscope system 10 can use light of any color (including cases in which the wavelength, the wavelength range, or the spectrum is different) in each image capturing frame as the illumination light for correction operation and the illumination light for main operation and can acquire any number of endoscope images. In this case, the image acquiring unit 54 acquires the correction-value-calculation image and the biological-information-calculation image as endoscope images. Subsequently, the correction-value calculating unit 72 can calculate the correction value by using the correction-value-calculation image among these endoscope images, and the index-value calculating unit 75 can calculate the index value by using the biological-information-calculation image among these endoscope images.

Figure 19:
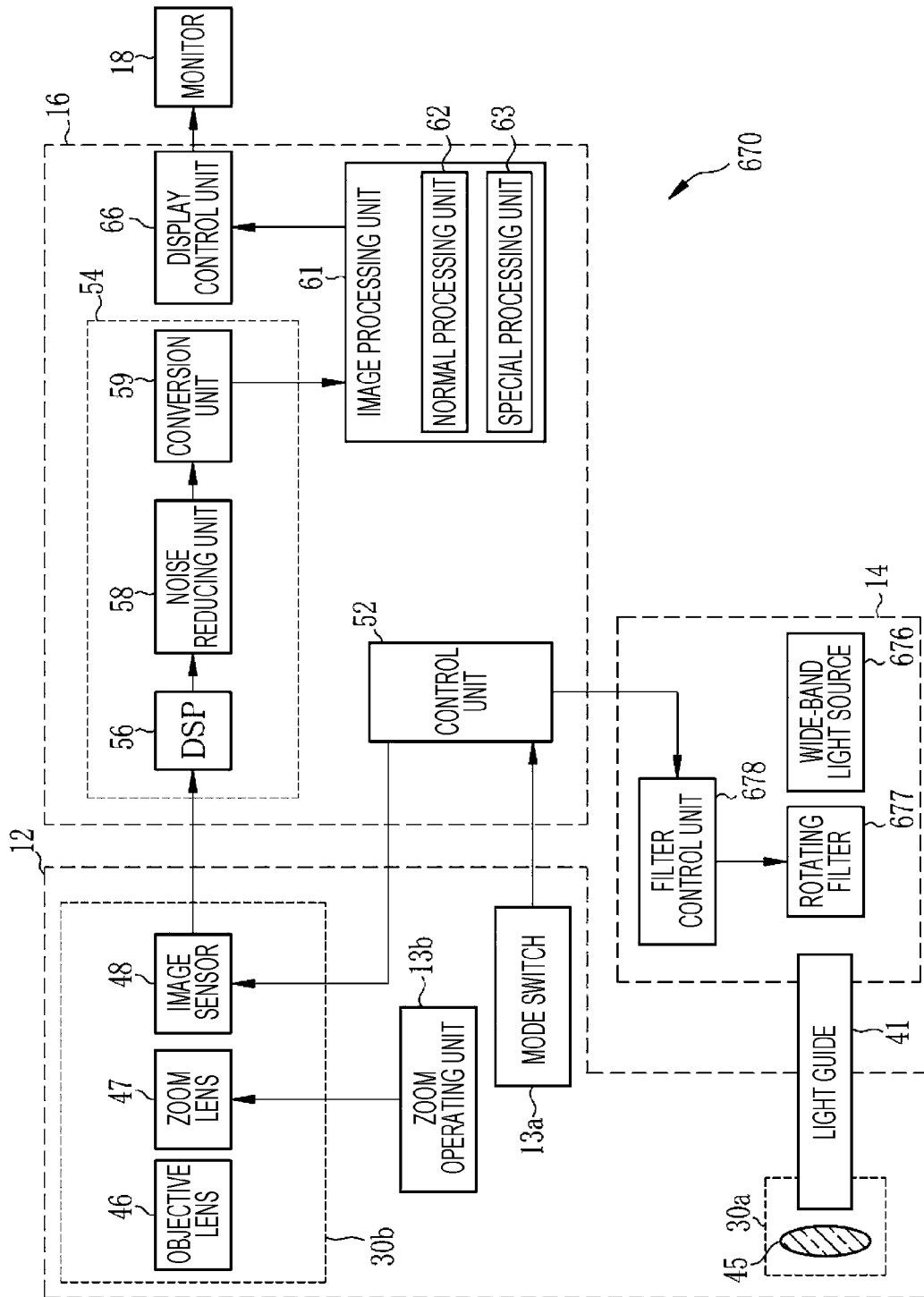
FIG. 19 is a block diagram of an endoscope system in a modification example.

In the above first to third embodiments, the light source unit 20 has the plurality of light sources 20a to 20d and forms illumination light by superimposing light emitted from these. However, as another example, the light source unit 20 can form the illumination light by extracting a part of components from light emitted from a wide-band light source for use. For example, an endoscope system 670 illustrated in FIG. 19 includes, instead of the light sources 20a to 20d and the light source control unit 22 in the first embodiment, a wide-band light source 676, a rotating filter 677, and a filter control unit 678 in the light source unit 20. In addition, in the endoscope system 670, the image sensor 48 is a monochrome sensor in which a color filter is not provided. Except for that, the endoscope system 670 is the same as the endoscope system 10 in the first to third embodiments.

The wide-band light source 676 is a xenon lamp, a white LED, or the like and emits white light whose wavelength range is from blue to red. The rotating filter 677 is provided so as to freely rotate in the light path of the wide-band light source 676 to limit the range of white light emitted from the wide-band light source 676, and a part of components enters the light guide 41 as the illumination light. Accordingly, the rotating filter 677 is sectioned as appropriate, and each section is provided with, for example, an optical filter that transmits the first blue light BS, a filter that transmits the second blue light BL, a filter that transmits the green light G, and a filter that transmits the red light R. In addition, the filter control unit 678 controls the position and rotation of the rotating filter 677 in accordance with the observation mode and the image capturing frame. Thus, as in the first embodiment or the like, it is possible to obtain the B1 image, the B2 image, the G image, and the R image in a case of the special observation mode, and to obtain the B image, the G image, and the R image in a case of the normal observation mode.

Figure 20:
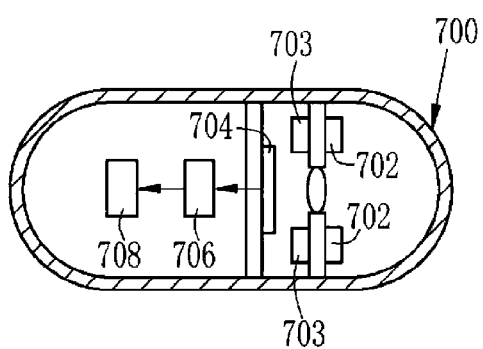
FIG. 20 is a schematic diagram of a capsule endoscope.

Although the present invention is implemented in the endoscope system that enables observation by inserting the endoscope 12 provided with the image sensor 48 into a subject in the above first to third embodiments, the present invention is also suitably used for a capsule endoscope system. As illustrated in FIG. 20, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 serves in substantially the same manner as the light source control unit 22 and the control unit 52. In addition, the control unit 703 can wirelessly communicate with the processor device of the capsule endoscope system by using the transmission/reception antenna 708. The processor device of the capsule endoscope system is substantially the same as the processor device 16 according to the above first to third embodiments, but the image processing unit 706 corresponding to the image acquiring unit 54 and the image processing unit 61 is provided in the capsule endoscope 700, and a generated observation image such as an oxygen-saturation-level image is transmitted to the processor device through the transmission/reception antenna 708. The image sensor 704 is configured in substantially the same manner as the image sensor 48.

In the above first to third embodiments, the correction operation is executed when the observation mode is switched from the normal observation mode to the special observation mode. However, the correction operation can be executed at any timing other than the timing at which the observation mode is switched to the special observation mode. For example, the correction operation can be forcibly executed in response to an input operation from the console 19 or the like. This function is useful when re-correction is wished at a given timing.

In the above first to third embodiments, the image acquiring unit 54 acquires a plurality of endoscope images of the observation target captured at different timings, the correction-value calculating unit 72 calculates a correction value by using the plurality of endoscope images, and the index-value calculating unit 75 calculates the index value 102 by using the plurality of endoscope images. This is because the special observation mode in the first to third embodiments is the oxygen-saturation-level observation mode. For example, in a case in which the oxygen-saturation-level observation mode is performed in another embodiment, or in a case in which the special observation mode is other than the oxygen-saturation-level observation mode, in accordance with the actual embodiment of the special observation mode, the image acquiring unit 54 can acquire a single endoscope image during the correction operation, and the correction-value calculating unit 72 can calculate a correction value by using the single endoscope image. In addition, even in a case in which the image acquiring unit 54 acquires a plurality of endoscope images of the observation target captured at different timings as in the first to third embodiments and in which the correction-value calculating unit 72 calculates a correction value by using the plurality of endoscope images, the index-value calculating unit 75 can calculate the index value 102 by using a single endoscope image among the plurality of endoscope images acquired by the image acquiring unit 54.

REFERENCE SIGNS LIST

10, 670 endoscope system
12 endoscope
12a insertion part
12b operating unit
12c bending part
12d tip part
12e angle knob
13a switch
13b zoom operating unit
14 light source device
16 processor device
18 monitor
19 console
20 light source unit
20a BS light source
20b BL light source
20c G light source
20d R light source
22 light source control unit
30a illumination optical system
30b imaging optical system
41 light guide
45 illumination lens
46 objective lens
47 zoom lens
48, 704 image sensor
52, 703 control unit
54 image acquiring unit
56 DSP
58 noise reducing unit
59 conversion unit
61, 706 image processing unit
62 normal processing unit
63 special processing unit
66 display control unit
71 special-observation-image generating unit
72 correction-value calculating unit
73 correction unit
74 input unit
75 index-value calculating unit
81 computation-value calculating unit
82 data storage unit
83 oxygen-saturation-level calculating unit
84 image generating unit
93, 94 isopleth
96, 97 graph
101 normal observation image
102 index value
102A first index value
102B second index value
102C third index value
103 correction execution button
104 pointer
110 oxygen-saturation-level image
111 indicator 201 determination unit
202, 202A, 202B, 202C determination result
301 improvement instructing unit
302 improvement instruction
303 result of improvement determination
676 wide-band light source
677 rotating filter
678 filter control unit
700 capsule endoscope
702 light source unit
708 transmission/reception antenna

What is claimed is:

1. An endoscope system comprising:
a processor configured to:
  acquire an endoscope image of an observation target captured by an endoscope;
  calculate, by using the endoscope image, a correction value of the endoscope image, biological information to be calculated by using the endoscope image, or data to be used for calculation of the biological information;
  calculate, by using the endoscope image, at least one index value to be used as a determination reference for determining whether the correction value is to be calculated or whether the correction value is to be used;
a display that displays the at least one index value; and
an input unit that inputs an instruction for calculating the correction value or an instruction for executing correction of the endoscope image, the biological information, or the data by using the correction value,
wherein the input unit is an input screen displayed on the display or an operating unit comprising an angle knob;
wherein, if the processor calculates the correction value in response to the instruction for calculating the correction value or if the instruction for executing correction is issued, the processor corrects the endoscope mage, the biological information, or the data by using the correction value, wherein
the processor determines, by using the at least one index value, whether the correction value is to be calculated or whether the correction value is to be used,
the display displays a result of determination of the processor in addition to the at least one index value, and
if the processor determines that the correction value is not to be calculated or that the correction value is not to be used, the processor causes the display to display an improvement instruction regarding image capturing conditions for the endoscope image,
wherein the at least one index value comprises a plurality of index values, wherein, if the processor calculates the plurality of index values, the processor determines, for each of the plurality of index values, whether the correction value is to be calculated or whether the corection value is to be used, and the display displays a result of determination of the processor together with each of the plurality of index values,
wherein, if the processor determines that the correction value is not to be calculated or that the correction value is not to be used, the processor causes the display to display an improvement instruction regarding image capturing conditions for the endoscope image,
wherein, after the improvement instruction has been displayed, the processor performs improvement determination for determining whether the image capturing conditions have been improved and causes the display to display a result of the improvement determination,
wherein the processor acquires a plurality of endoscope images of the observation target captured by the endoscope at different timings, wherein the processor calculates the correction value by using the plurality of endoscope images, and wherein the processor calculates the at least one index value by using one or more of the plurality of endoscope images.

2. The endoscope system according to claim 1,
wherein, after the improvement instruction has been displayed, the processor performs improvement determination for determining whether the image capturing conditions have been improved and causes the display to display a result of the improvement determination.

3. The endoscope system according to claim 1,
wherein the processor acquires a plurality of endoscope images of the observation target captured by the endoscope at different timings,
wherein the processor calculates the correction value by using the plurality of endoscope images, and
wherein the processor calculates the at least one index value by using one or more of the plurality of endoscope images.

4. The endoscope system according to claim 3,
wherein the processor changes illumination light or irradiation conditions of the illumination light and acquires the plurality of endoscope images of the observation target captured at different timings.

5. The endoscope system according to claim 4,
wherein the processor acquires, as the plurality of endoscope images, a correction-value-calculation image to be used for calculation of the correction value and a biological-information-calculation image to be used for calculation of the biological information,
wherein the processor calculates the correction value by using the correction-value-calculation image among the plurality of endoscope images, and
wherein the processor calculates the at least one index value by using the correction-value-calculation image among the plurality of endoscope images.

6. The endoscope system according to claim 4,
wherein the processor acquires, as one of the plurality of endoscope images, a biological-information-calculation image to be used for calculation of the biological information,
wherein the processor calculates the correction value by using the biological-information-calculation image, and
wherein the processor calculates the at least one index value by using the used biological-information-calculation image for calculating the correction value.

7. The endoscope system according to claim 3,
wherein the processor calculates the at least one index value of a movement amount of the observation target compared between the plurality of endoscope images, of a movement amount of the observation target in one of the plurality of endoscope images, or of brightness, a pixel value, presence or absence of an attached matter, or an amount of the attached matter.

8. The endoscope system according to claim 1, wherein the processor changes illumination light or irradiation conditions of the illumination light and acquires the plurality of endoscope images of the observation target captured at different timings.

9. The endoscope system according to claim 8,
wherein the processor acquires, as one of the plurality of endoscope images, a biological-information-calculation image to be used for calculation of the biological information,
wherein the processor calculates the correction value by using the biological-information-calculation image, and
wherein the processor calculates the at least one index value by using the used biological-information-calculation image for calculating the correction value.

10. An endoscope system comprising:
a processor configured to:
acquire an endoscope image of an observation target captured by an endoscope;
calculate, by using the endoscope image, a correction value of the endoscope image, biological information to be calculated by using the endoscope image, or data to be used for calculation of the biological information;
calculate, by using the endoscope image, at least one index value to be used as a determination reference for determining whether the correction value is to be calculated or whether the correction value is to be used;
a display that displays the at least one index value; and
an input unit that inputs an instruction for calculating the correction value or an instruction for executing correction of the endoscope image, the biological information, or the data by using the correction value, wherein the input unit is an input screen displayed on the display or an operating unit comprising an angle knob;
wherein, if the processor calculates the correction value in response to the instruction for calculating the correction value or if the instruction for executing correction is issued, the processor corrects the endoscope image, the biological information, or the data by using the correction value; wherein the processor determines, by using the at least one index value, whether the correction value is to be calculated or whether the correction value is to be used;
wherein, if the processor determines that the correction value is not to be calculated or that the correction value is not to be used, the processor causes the display to display an improvement instruction regarding image capturing conditions for the endoscope image,
wherein the display displays a result of determination of the processor in addition to the at least one index value,
wherein the at least one index value comprises a plurality of index values,
wherein, if the processor calculates the plurality of index values, the processor determines, for each of the plurality of index values, whether the correction value is to be calculated or whether the correction value is to be used, and the display displays a result of determination of the processor together with each of the plurality of index values,
wherein, after the improvement instruction has been displayed, the processor performs improvement determination for determining whether the image capturing conditions have been improved and causes the display to display a result of the improvement determination,
wherein the processor acquires a plurality of endoscope images of the observation target captured by the endoscope at different timings,
wherein the processor calculates the correction value by using the plurality of endoscope images,
wherein the processor calculates the at least one index value by using one or more of the plurality of endoscope images,
wherein the processor changes illumination light or irradiation conditions of the illumination light and acquires the plurality of endoscope images of the observation target captured at different timings,
wherein the processor acquires, as one of the plurality of endoscope images, a biological-information-calculation image to be used for calculation of the biological information,
wherein the processor calculates the correction value by using the biological-information-calculation image,
wherein the processor calculates the at least one index value by using the used biological-information-calculation image for calculating the correction value, and
wherein the processor calculates the at least one index value of a movement amount of the observation target compared between the plurality of endoscope images, of a movement amount of the observation target in one of the plurality of endoscope images, or of brightness, a pixel value, presence or absence of an attached matter, or an amount of the attached matter.

11. A processor device comprising:
a processor configured to:
acquire an endoscope image of an observation target captured by an endoscope;
calculate, by using the endoscope image, a correction value of the endoscope image, biological information to be calculated by using the endoscope image, or data to be used for calculation of the biological information;
calculate, by using the endoscope image, at least one index value to be used as a determination reference for determining whether the correction value is to be calculated or whether the correction value is to be used;
cause a display to display the at least one index value;
wherein, if the processor calculates the correction value in response to an instruction for calculating the correction value or if an instruction for executing correction is issued, the processor corrects the endoscope image, the biological information, or the data by using the correction value, wherein
the processor determines, by using the at least one index value, whether the correction value is to be calculated or whether the correction value is to be used,
the display displays a result of determination of the processor in addition to the at least one index value, and
if the processor determines that the correction value is not to be calculated or that the correction value is not to be used, the processor causes the display to display an improvement instruction regarding image capturing conditions for the endoscope image,
wherein the at least one index value comprises a plurality of index values, wherein, if the processor calculates the plurality of index values, the processor determines, for each of the plurality of index values, whether the correction value is to be calculated or whether the correction value is to be used, and the display displays a result of determination of the processor together with each of the plurality of index values,
wherein, if the processor determines that the correction value is not to be calculated or that the correction value is not to be used, the processor causes the display to display an improvement instruction regarding image capturing conditions for the endoscope image, wherein, after the improvement instruction has been displayed, the processor performs improvement determination for determining whether the image capturing conditions have been improved and causes the display to display a result of the improvement determination, wherein the processor acquires a plurality of endoscope images of the observation target captured by the endoscope at different timings, wherein the processor calculates the correction value by using the plurality of endoscope images, and wherein the processor calculates the at least one index value by usino one or more of the plurality of endoscope images.

12. A method for operating an endoscope system haying a processor and a display, the method comprising:

a step in which the processor acquires an endoscope image of an observation target captured by an endoscope;

a step in which the processor calculates, by using the endoscope image, a correction value of the endoscope image, biological information to be calculated by using the endoscope image, or data to be used for calculation of the biological information;

a step in which the processor calculates, by using the endoscope image, at least one index value to be used as a determination reference for determining whether the correction value is to be calculated or whether the correction value is to be used;

a step in which the display displays the at least one index value; and a step in which, if the processor calculates the correction value in response to an instruction for calculating the correction value or if an instruction for executing correction is issued, the processor corrects the endoscope image, the biological information, or the data by using the correction value, wherein the processor determines, by using the at least one index value, whether the correction value is to be calculated or whether the correction value is to be used, the display displays a result of determination of the processor in addition to the at least one index value, and if the processor determines that the correction value is not to be calculated or that the correction value is not to be used, the processor causes the display to display an improvement instruction regarding image capturing conditions for the endoscope image, a step in which the at least one index value comprises a plurality of index values, wherein, if the processor calculates the plurality of index values, the processor determines, for each of the plurality of index values, whether the correction value is to be calculated or whether the correction value is to be used, and the display displays a result of determination of the processor together with each of the plurality of index values, a step in which, if the processor determines that the correction value is not to be calculated or that the correction value is not to be used, the erocessor causes the display to display an improvement instruction regarding image capturing conditions for the endoscope image, a step in which, after the improvement instruction has been displayed, the processor performs improvement determination for determining whether the image capturing conditions have been improved and causes the display to display a result of the improvement determination, a step in which the processor acquires a plurality of endoscope images of the observation target captured by the endoscope at different timings, wherein the processor calculates the correction value by using the plurality of endoscope images, and wherein the processor calculates the at least one index value by using one or more of the plurality of endoscope images.

* * * * *